(12) United States Patent
Feldman et al.

(10) Patent No.: US 9,478,757 B2
(45) Date of Patent: Oct. 25, 2016

(54) BLUE LUMINESCENT COMPOUNDS

(71) Applicant: E I DU PONT DE NEMOURS AND COMPANY, Wilmington, DE (US)

(72) Inventors: Jerald Feldman, Wilmington, DE (US); Kerwin D Dobbs, Wilmington, DE (US); Troy C Gehret, Wilmington, DE (US); Charles D McLaren, Landenberg, PA (US); Giang Dong Vo, Wilmington, DE (US); Ying Wang, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 229 days.

(21) Appl. No.: 14/190,455

(22) Filed: Feb. 26, 2014

(65) Prior Publication Data
US 2015/0243909 A1 Aug. 27, 2015

(51) Int. Cl.
H01L 51/54 (2006.01)
C09K 11/06 (2006.01)
C07D 249/08 (2006.01)
H01L 51/00 (2006.01)
C07F 15/00 (2006.01)
H01L 51/50 (2006.01)

(52) U.S. Cl.
CPC ......... *H01L 51/0085* (2013.01); *C07D 249/08* (2013.01); *C07F 15/0033* (2013.01); *C09K 11/06* (2013.01); *C09K 2211/1059* (2013.01); *C09K 2211/185* (2013.01); *H01L 51/5012* (2013.01); *H01L 51/5016* (2013.01)

(58) Field of Classification Search
USPC ..................................................... 548/269.4
See application file for complete search history.

(56) References Cited

U.S. PATENT DOCUMENTS

| | | | | |
|---|---|---|---|---|
| 2006/0251923 A1* | 11/2006 | Lin et al. | ............ | C07F 15/0046 428/690 |
| 2007/0085073 A1* | 4/2007 | Inoue et al. | ........ | C07F 15/0046 257/40 |
| 2009/0102370 A1* | 4/2009 | Taka et al. | ........... | C07D 233/58 313/504 |
| 2013/0221278 A1* | 8/2013 | Inoue et al. | ........ | C07F 15/0033 252/301.16 |

* cited by examiner

*Primary Examiner* — Marie R. Yamnitzky

(57) ABSTRACT

There is provided a compound having Formula II

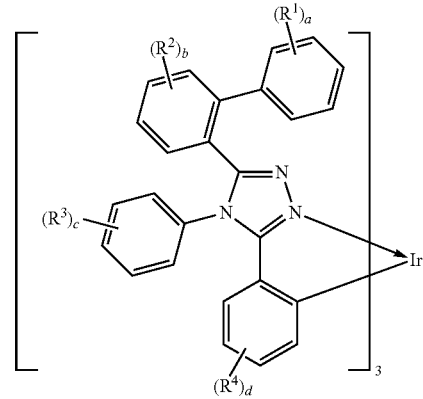

Formula II

In Formula II: $R^1$-$R^4$ are the same or different at each occurrence and can be D, alkyl, silyl, aryl, deuterated alkyl, deuterated silyl, or deuterated aryl; a and c are the same or different and are an integer from 0-5; and b and d are the same or different and are an integer from 0-4.

17 Claims, 2 Drawing Sheets

BLUE LUMINESCENT COMPOUNDS

BACKGROUND INFORMATION

1. Field of the Disclosure

This disclosure relates in general to blue luminescent compounds and their use in electronic devices.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a compound having Formula I

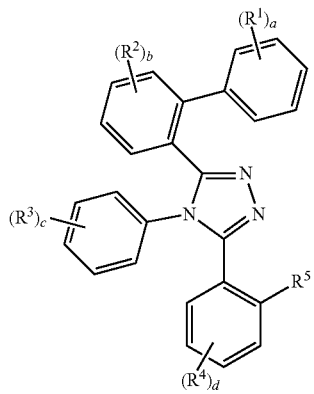

Formula I wherein:
$R^1$-$R^4$ are the same or different at each occurrence and are selected from the group consisting of D, alkyl, silyl, aryl, deuterated alkyl, deuterated silyl, and deuterated aryl;
$R^5$ is H or D;
a and c are the same or different and are an integer from 0-5; and
b and d are the same or different and are an integer from 0-4.

There is also provided a material having Formula II

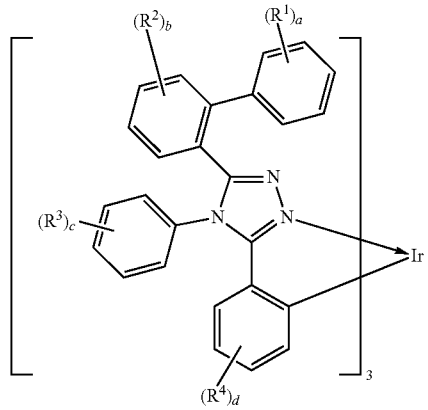

Formula II wherein:
$R^1$-$R^4$ are the same or different at each occurrence and are selected from the group consisting of D, alkyl, silyl, aryl, deuterated alkyl, deuterated silyl, and deuterated aryl;
a and c are the same or different and are an integer from 0-5; and
b and d are the same or different and are an integer from 0-4.

There is also provided an organic electronic device comprising a first electrical contact, a second electrical contact and a photoactive layer there between, the photoactive layer comprising the material having Formula II.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
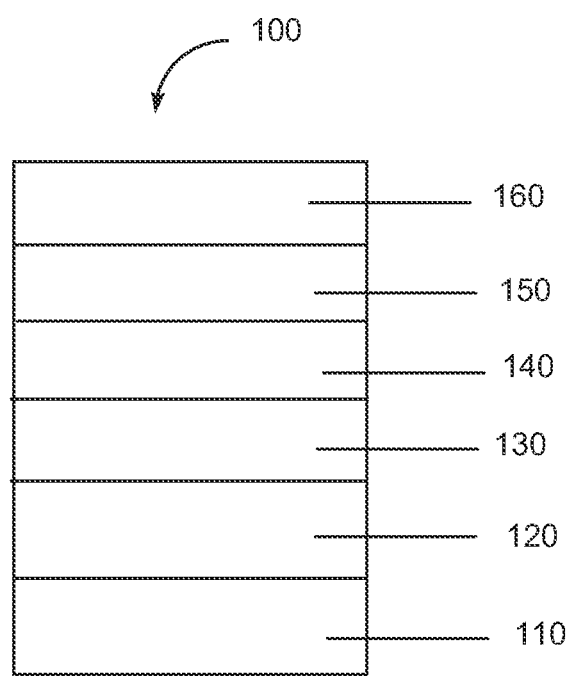
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Material Having Formula I or Formula II, Synthesis, Devices, and finally Examples.

1. Definitions and Clarification of Terms

Before addressing details of embodiments described below, some terms are defined or clarified.

The term "alkyl" is intended to mean a group derived from an aliphatic hydrocarbon and includes a linear, a branched, or a cyclic group. In some embodiments, an alkyl has from 1-20 carbon atoms.

The term "anti-quenching" when referring to a layer or material, refers to such layer or material which prevents quenching of blue luminance by the electron transport layer, either via an energy transfer or an electron transfer process.

The term "aromatic compound" is intended to mean an organic compound comprising at least one unsaturated cyclic group having delocalized pi electrons. The aromatic ring has 4n+2 pi electrons and is essentially planar.

The term "aryl" is intended to mean a group derived from an aromatic hydrocarbon having one point of attachment. The term includes groups which have a single ring and those which have multiple rings which can be joined by a single bond or fused together. The term is intended to include both hydrocarbon aryls, having only carbon in the ring structure, and heteroaryls. The term "alkylaryl" is intended to mean an aryl group having one or more alkyl substituents. In some embodiments, a hydrocarbon aryl has 6-60 ring carbons. In some embodiments, a heteroaryl has 3-60 ring carbons.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen has been replaced by deuterium, abbreviated herein as "D". The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell).

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

All groups may be unsubstituted or substituted. The substituent groups are discussed below.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds Having Formula I or Formula II

There is provided herein a new compound having Formula I

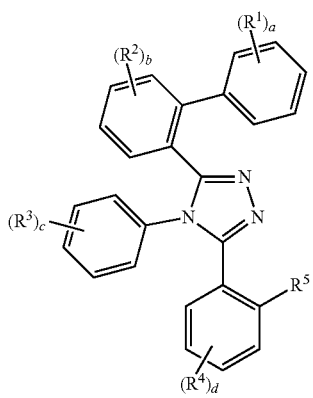

Formula I wherein:
$R^1$-$R^4$ are the same or different at each occurrence and are selected from the group consisting of D, alkyl, silyl, aryl, deuterated alkyl, deuterated silyl, and deuterated aryl;
$R^5$ is H or D;
a and c are the same or different and are an integer from 0-5; and
b and d are the same or different and are an integer from 0-4.

The new compounds having Formula I can be used as ligands to form metal complexes having Formula II

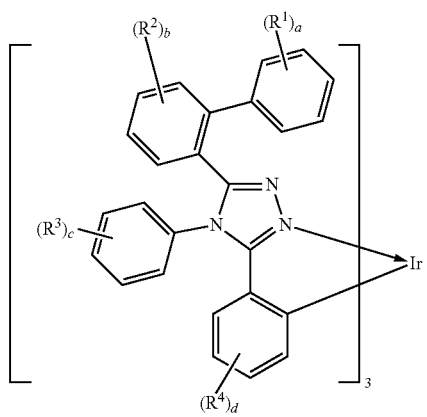

Formula II wherein:
$R^1$-$R^4$ are the same or different at each occurrence and are selected from the group consisting of D, alkyl, silyl, aryl, deuterated alkyl, deuterated silyl, and deuterated aryl;
a and c are the same or different and are an integer from 0-5; and
b and d are the same or different and are an integer from 0-4.

In some embodiments, the compounds having Formula II are useful as emissive materials. The compound having Formula II are capable of blue electroluminescence. The compounds can be used alone or as a dopant in a host material.

The compounds having Formula II are soluble in many commonly used organic solvents. Solutions of these compounds can be used for liquid deposition using techniques such as discussed above. Surprisingly, it has been found that the compounds having a phenyl group in the position indicated below as "A" have an unexpected shift in emission toward blue.

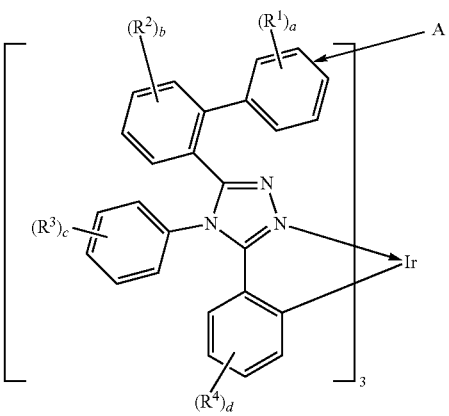

The shift toward blue can be seen as a decrease in the wavelength of the peak of maximum emission. The shift toward blue can be seen as a decrease in the color coordinates of emission, according to the chromaticity scale.

In some embodiments, the compounds have an electroluminescent ("EL") peak less than 500 nm. In some embodiments, the compounds have an EL peak in the range of 445-490 nm. In some embodiments, the compounds used in devices result in color coordinates of x<0.25 and y<0.5, according to the 1931 C.I.E. convention (Commission Internationale de L'Eclairage, 1931). In some embodiments, the color coordinates are x<0.20 and y<0.4; in some embodiments, x<0.18 and y<0.35.

Also surprisingly, such compounds provide other advantages in electronic devices. In some embodiments, devices made with compounds having Formula II have improved efficiencies and lifetimes. This is advantageous for reducing energy consumption in all types of devices, and particularly for lighting applications. Higher efficiency also improves device lifetime at constant luminance.

Specific embodiments of the present invention include, but are not limited to, the following.

In some embodiments, the compound of Formula I or Formula II is deuterated.

In some embodiments, the compound of Formula I or Formula II is at least 10% deuterated. By "% deuterated" or "% deuteration" is meant the ratio of deuterons to the total of hydrogens plus deuterons, expressed as a percentage. The deuteriums may be on the same or different groups.

In some embodiments, the compound of Formula I or Formula II is at least 25% deuterated.

In some embodiments, the compound of Formula I or Formula II is at least 50% deuterated.

In some embodiments, the compound of Formula I or Formula II is at least 75% deuterated.

In some embodiments, the compound of Formula I or Formula II is at least 90% deuterated.

In some embodiments of the compound of Formula I or Formula II, a>0 and at least one $R^1$ is an unsubstituted alkyl or unsubstituted deuterated alkyl having 1-6 carbons.

In some embodiments of the compound of Formula I or Formula II, a>0 and at least one $R^1$ is an unsubstituted alkyl or unsubstituted deuterated alkyl having 1-3 carbons.

In some embodiments of the compound of Formula I or Formula II, a>0 and at least one $R^1$ is a silyl or deuterated silyl having 3-6 carbons.

In some embodiments of the compound of Formula I or Formula II, a>0 and at least one $R^1$ is an aryl or deuterated aryl having 6-18 ring carbons.

In some embodiments of the compound of Formula I or Formula II, a>0 and at least one $R^1$ is selected from the group consisting of phenyl, naphthyl, biphenyl, and deuterated analogs thereof.

In some embodiments of the compound of Formula I or Formula II, a>0 and $R^1$ is an alkylaryl or deuterated alkylaryl having 6-20 carbons.

In some embodiments of the compound of Formula I or Formula II, a=0.

In some embodiments of the compound of Formula I or Formula II, a=1.

In some embodiments of the compound of Formula I or Formula II, a=2.

In some embodiments of the compound of Formula I or Formula II, a=2 and the $R^1$ groups are meta to each other.

In some embodiments of the compound of Formula I or Formula II, b>0 and at least one $R^2$ is an unsubstituted alkyl or unsubstituted deuterated alkyl having 1-6 carbons.

In some embodiments of the compound of Formula I or Formula II, b>0 and at least one $R^2$ is an unsubstituted alkyl or unsubstituted deuterated alkyl having 1-3 carbons.

In some embodiments of the compound of Formula I or Formula II, b>0 and at least one $R^2$ is a silyl or deuterated silyl having 3-6 carbons.

In some embodiments of the compound of Formula I or Formula II, b>0 and at least one $R^2$ is an aryl or deuterated aryl having 6-18 ring carbons.

In some embodiments of the compound of Formula I or Formula II, b>0 and at least one $R^2$ is selected from the group consisting of phenyl, naphthyl, biphenyl, and deuterated analogs thereof.

In some embodiments of the compound of Formula I or Formula II, b>0 and $R^2$ is an alkylaryl or deuterated alkylaryl having 6-20 carbons.

In some embodiments of the compound of Formula I or Formula II, b=0.

In some embodiments of the compound of Formula I or Formula II, b=1.

In some embodiments of the compound of Formula I or Formula II, b=2.

In some embodiments of the compound of Formula I or Formula II, b=2 and the $R^2$ groups are meta to each other.

In some embodiments of the compound of Formula I or Formula II, c>0 and at least one $R^3$ is an unsubstituted alkyl or unsubstituted deuterated alkyl having 1-6 carbons.

In some embodiments of the compound of Formula I or Formula II, c>0 and at least one $R^3$ is an unsubstituted alkyl or unsubstituted deuterated alkyl having 1-3 carbons.

In some embodiments of the compound of Formula I or Formula II, c>0 and at least one $R^3$ is a branched alkyl or deuterated branched alkyl having 3-8 carbons; in some embodiments, a branched alkyl or deuterated branched alkyl having 3-6 carbons.

In some embodiments of the compound of Formula I or Formula II, c>0 and at least one $R^3$ is a silyl or deuterated silyl having 3-6 carbons.

In some embodiments of the compound of Formula I or Formula II, c>0 and at least one $R^3$ is an aryl or deuterated aryl having 6-18 ring carbons.

In some embodiments of the compound of Formula I or Formula II, c>0 and at least one $R^3$ is selected from the group consisting of phenyl, naphthyl, biphenyl, and deuterated analogs thereof.

In some embodiments of the compound of Formula I or Formula II, c>0 and $R^3$ is an alkylaryl or deuterated alkylaryl having 6-20 carbons.

In some embodiments of the compound of Formula I or Formula II, c=0.

In some embodiments of the compound of Formula I or Formula II, c=1.

In some embodiments of the compound of Formula I or Formula II, c=2.

In some embodiments of the compound of Formula I or Formula II, c=2 and the $R^3$ groups are meta to each other.

In some embodiments of the compound of Formula I or Formula II, c=1 or 2.

In some embodiments of the compound of Formula I or Formula II, d>0 and at least one $R^4$ is an unsubstituted alkyl or unsubstituted deuterated alkyl having 1-6 carbons.

In some embodiments of the compound of Formula I or Formula II, d>0 and at least one $R^4$ is an unsubstituted alkyl or unsubstituted deuterated alkyl having 1-3 carbons.

In some embodiments of the compound of Formula I or Formula II, d>0 and at least one $R^4$ is a silyl or deuterated silyl having 3-6 carbons.

In some embodiments of the compound of Formula I or Formula II, d>0 and at least one $R^4$ is an aryl or deuterated aryl having 6-18 ring carbons.

In some embodiments of the compound of Formula I or Formula II, d>0 and at least one $R^4$ is selected from the group consisting of phenyl, naphthyl, biphenyl, and deuterated analogs thereof.

In some embodiments of the compound of Formula I or Formula II, d>0 and $R^4$ is an alkylaryl or deuterated alkylaryl having 6-20 carbons.

In some embodiments of the compound of Formula I or Formula II, d=0.

In some embodiments of the compound of Formula I or Formula II, d=1.

In some embodiments of the compound of Formula I or Formula II, d=2.

In some embodiments of the compound of Formula I or Formula II, d=2 and the $R^4$ groups are meta to each other.

Any of the above embodiments can be combined with one or more of the other embodiments, so long as they are not mutually exclusive. For example, the embodiment in which $R^1$ is an alkyl or deuterated alkyl having 3-20 carbons can be combined with the embodiment in which $R^2$ is selected from the group consisting of methyl, propyl, butyl, and deuterated analogs thereof. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula I include, but are not limited to, the compounds shown below.
Compound L1
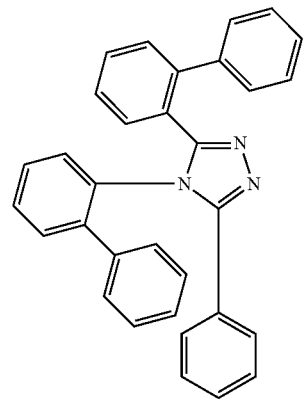
Compound L2
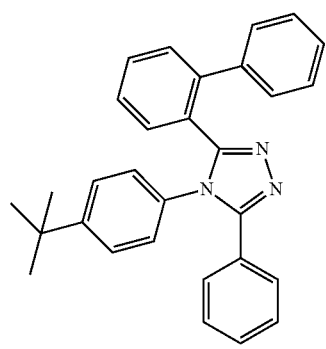
Compound L3
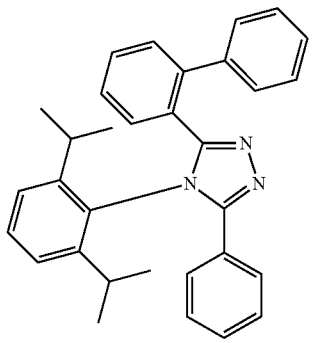
Compound L4
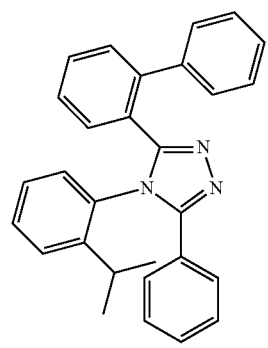
-continued
Compound L5
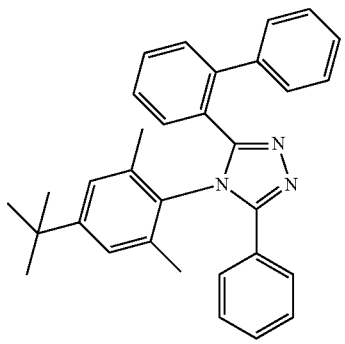
Compound L6
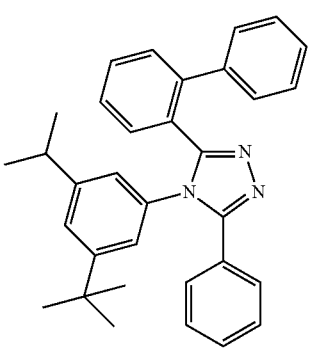
Compound L7
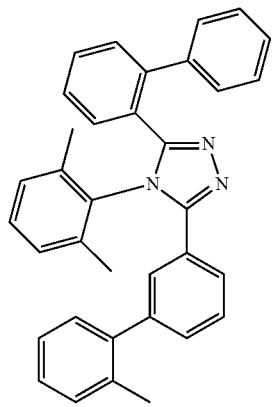
Compound L8
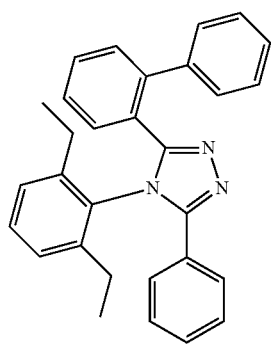

Compound L9
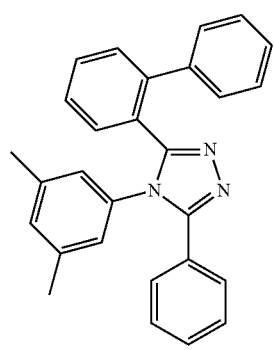
Compound L10
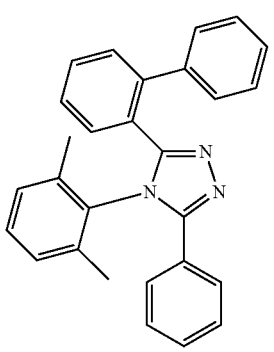
Examples of compounds having Formula II include, but are not limited to, the compounds shown below.
Compound B1
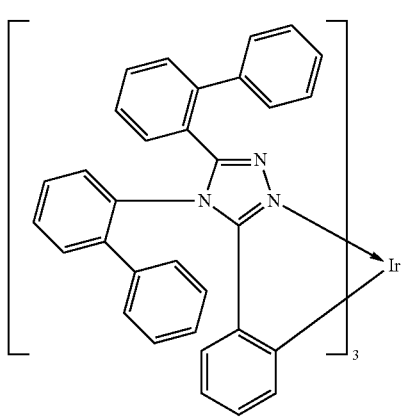
Compound B2
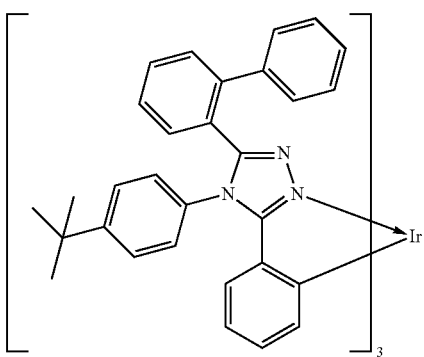
Compound B3
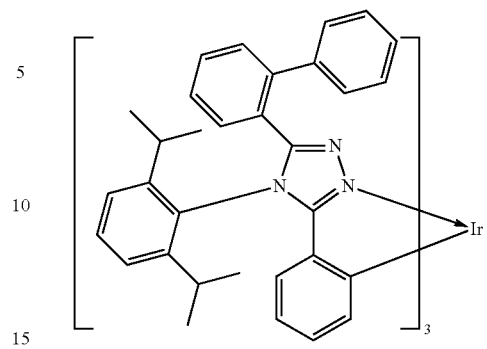
Compound B4
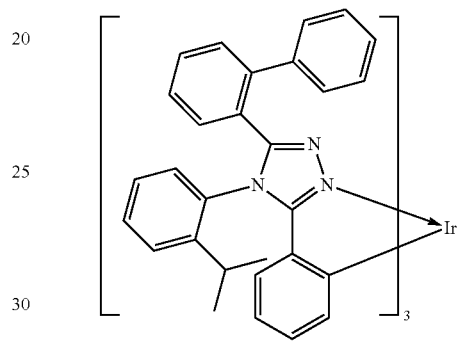
Compound B5
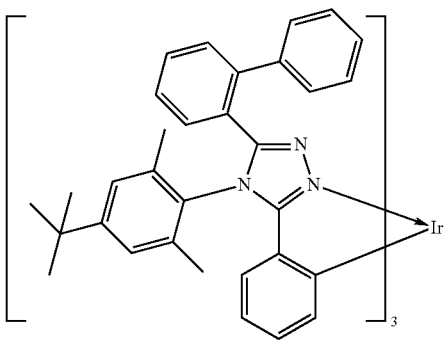
Compound B6
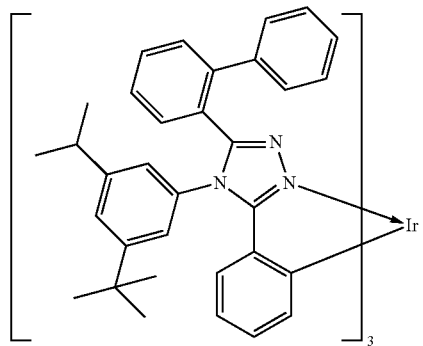

-continued

Compound B7

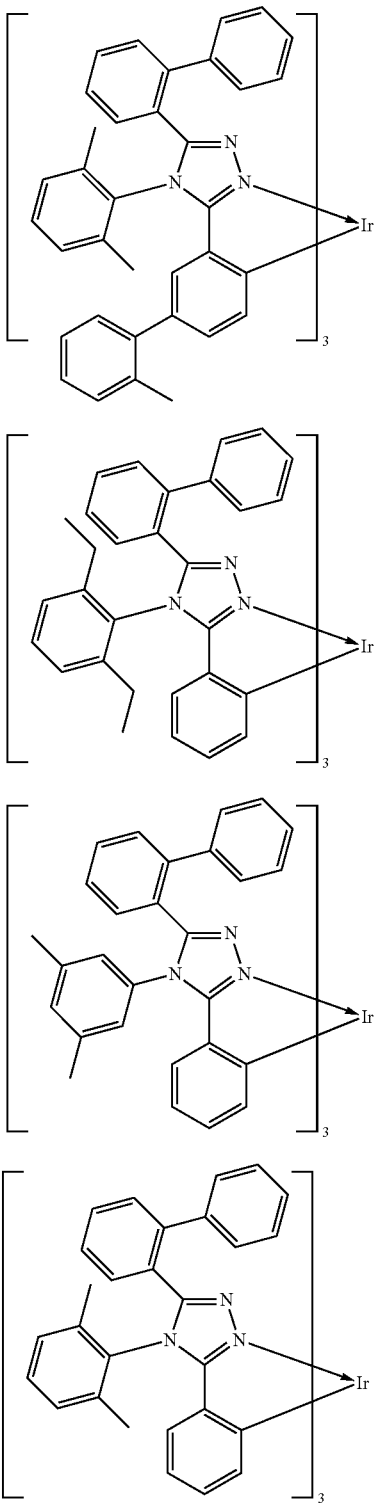

Compound B8

Compound B9

Compound B10

3. Synthesis

The compounds having Formula I described herein can be synthesized by a variety of procedures that have precedent in the literature. The exact procedure chosen will depend on a variety of factors, including availability of starting materials and reaction yield.

In one procedure (shown below), a 2-biphenylcarboxylic acid is allowed to react with oxalyl chloride in the presence of catalytic amounts of N,N-dimethylformamide (DMF). The resulting acyl chloride is then treated in situ with 5-phenyl-1H-tetrazole and pyridine at 100° C. to give a 2-(biphenyl-2-yl)-5-phenyl-1,3,4-oxadiazole, which is isolated. In the final step, an aniline is allowed to react with AlCl₃ and then treated with the 2-(biphenyl-2-yl)-5-phenyl-1,3,4-oxadiazole followed by 1-methyl-2-pyrrolidinone (NMP). The mixture is heated to reflux (internal temperature ~215° C.) to form a 3-([1,1'-biphenyl]-2-yl)-4,5-diphenyl-4H-1,2,4-triazole (Formula 1), which is isolated and purified.

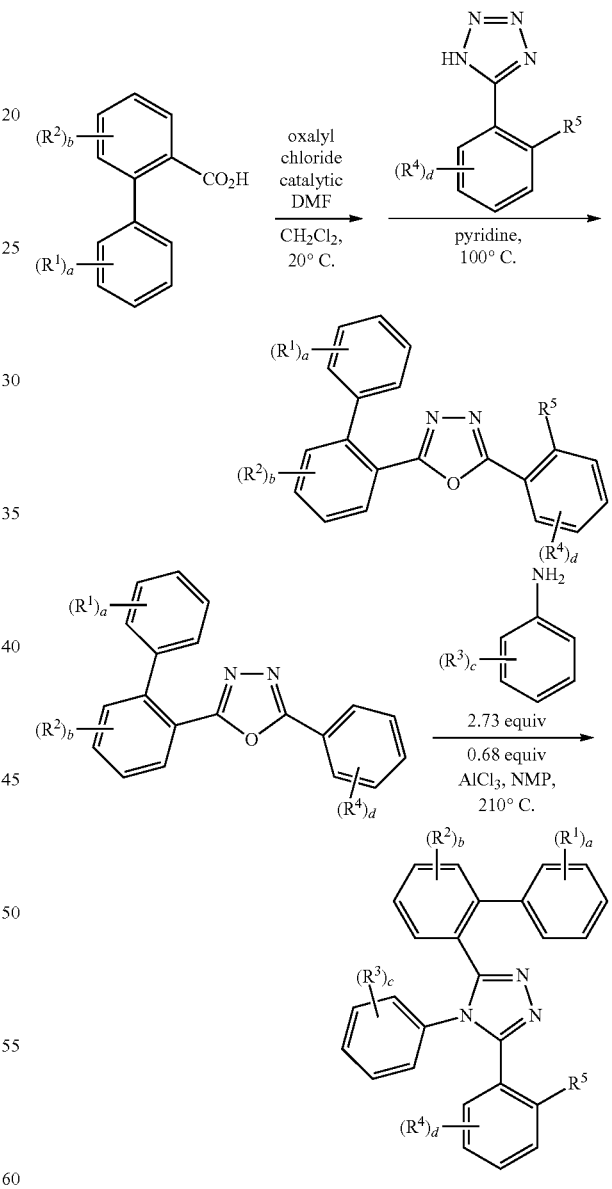

In another procedure (shown below), a 2-bromobenzohydrazide is allowed to react with triethyl orthoformate at 160° C. to form a 2-(2-bromophenyl)-1,3,4-oxadiazole. The isolated 2-(2-bromophenyl)-1,3,4-oxadiazole was allowed to react with an aniline in the presence of trifluoroacetic acid and o-dichlorobenzene at 185° C. to give a 3-(2-bromophenyl)-4-(phenyl)-4H-[1,2,4]triazole. This compound was isolated and coupled with a phenylboronic acid under Suzuki-Miyaura coupling conditions to afford a 3-biphenyl-2-yl-4-(phenyl)-4H-[1,2,4]triazole, which is isolated. N-Bromosuccinimide was treated with the 3-biphenyl-2-yl-4-(phenyl)-4H-[1,2,4]triazole to form a 3-biphenyl-2-yl-5-bromo-4-(phenyl)-4H-[1,2,4]triazole, which was isolated. In the last step, a phenylboronic acid was coupled with 3-biphenyl-2-yl-5-bromo-4-(phenyl)-4H-[1,2,4]triazole under Suzuki-Miyaura coupling conditions to afford a 3-([1,1'-biphenyl]-2-yl)-4,5-diphenyl-4H-1,2,4-triazole (Formula 1) which is isolated and purified.

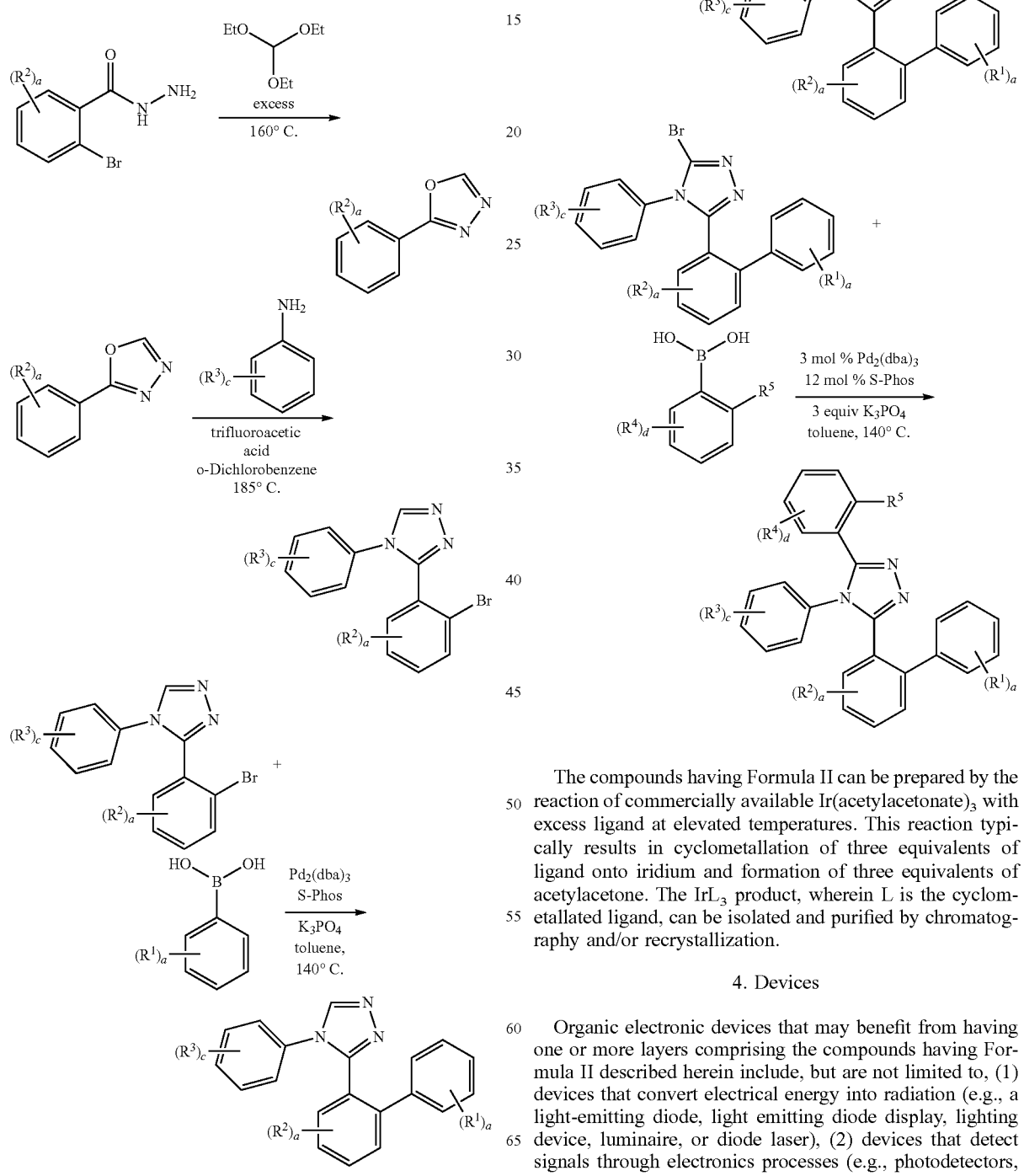

The compounds having Formula II can be prepared by the reaction of commercially available Ir(acetylacetonate)$_3$ with excess ligand at elevated temperatures. This reaction typically results in cyclometallation of three equivalents of ligand onto iridium and formation of three equivalents of acetylacetone. The IrL$_3$ product, wherein L is the cyclometallated ligand, can be isolated and purified by chromatography and/or recrystallization.

4. Devices

Organic electronic devices that may benefit from having one or more layers comprising the compounds having Formula II described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
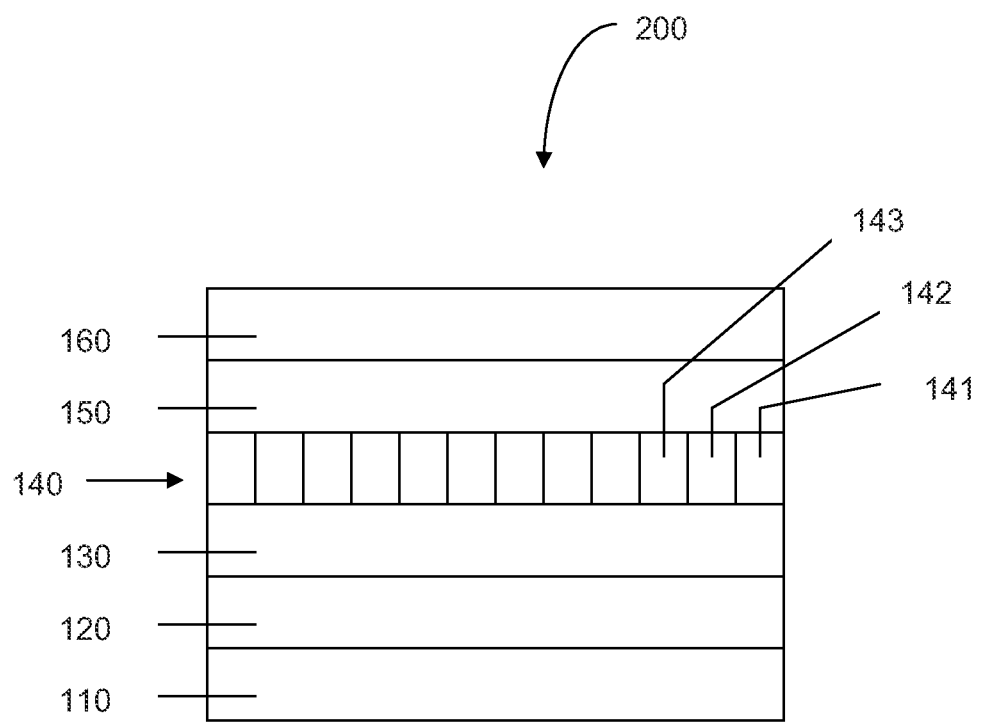
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula II are useful as the emissive material in photoactive layer 140, having blue emission color. They can be used alone or as a dopant in a host material.

a. Photoactive Layer

In some embodiments, the photoactive layer comprises a host material and a compound having Formula II as a dopant. In some embodiments, a second host material may be present. In some embodiments, the photoactive layer consists essentially of a host material and a compound having Formula II as a dopant. In some embodiments, the photoactive layer consists essentially of a first host material, a second host material, and a compound having Formula II as a dopant. The weight ratio of dopant to total host material is in the range of 5:95 to 70:30; in some embodiments, 10:90 to 20:80.

In some embodiments, the host has a triplet energy level higher than that of the dopant, so that it does not quench the emission. In some embodiments, the host is selected from the group consisting of carbazoles, indolocarbazoles, triazines, aryl ketones, phenylpyridines, pyrimidines, phenanthrolines, triarylamines, deuterated analogs thereof, combinations thereof, and mixtures thereof.

In some embodiments, the photoactive layer is intended to emit white light. In some embodiments, the photoactive layer comprises a host, a compound of Formula II, and one or more additional dopants emitting different colors, so that the overall emission is white. In some embodiments, the photoactive layer consists essentially of a host, a first dopant having Formula II, and a second dopant, where the second dopant emits a different color than the first dopant. In some embodiments, the emission color of the second dopant is yellow. In some embodiments, the photoactive layer consists essentially of a host, a first dopant having Formula II, a second dopant, and a third dopant. In some embodiments, the emission color of the second dopant is red and the emission color of the third dopant is green.

Any kind of electroluminescent ("EL") material can be used as second and third dopants. EL materials include, but are not limited to, small molecule organic fluorescent compounds, luminescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, arylamino derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red, orange and yellow light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

In some embodiments, the second and third dopants are cyclometallated complexes of Ir or Pt.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (—NPB), and porphyrinic compounds, such as copper phthalocyanine. In some embodiments, the hole transport layer comprises a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further comprises a p-dopant. In some embodiments, the hole transport layer is doped with a p-dopant. Examples of p-dopants include, but are not limited to, tetrafluorotetra-cyanoquinodimethane (F4-TCNQ) and perylene-3,4,9,10-tetracarboxylic-3,4,9,10-dianhydride (PTCDA).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An anti-quenching layer may be present between the photoactive layer and the electron transport layer to prevent quenching of blue luminance by the electron transport layer. To prevent energy transfer quenching, the triplet energy of the anti-quenching material has to be higher than the triplet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high triplet energy.

Examples of materials for the anti-quenching layer include, but are not limited to, triphenylene, triphenylene derivatives, carbazole, carbazole derivatives, and deuterated analogs thereof. Some specific materials include those shown below.

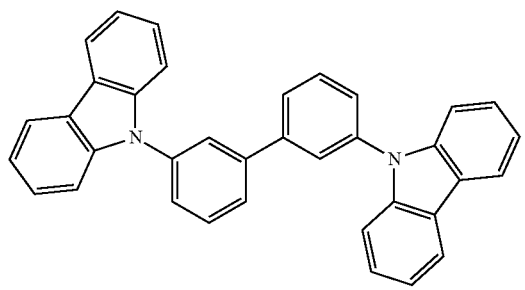

-continued

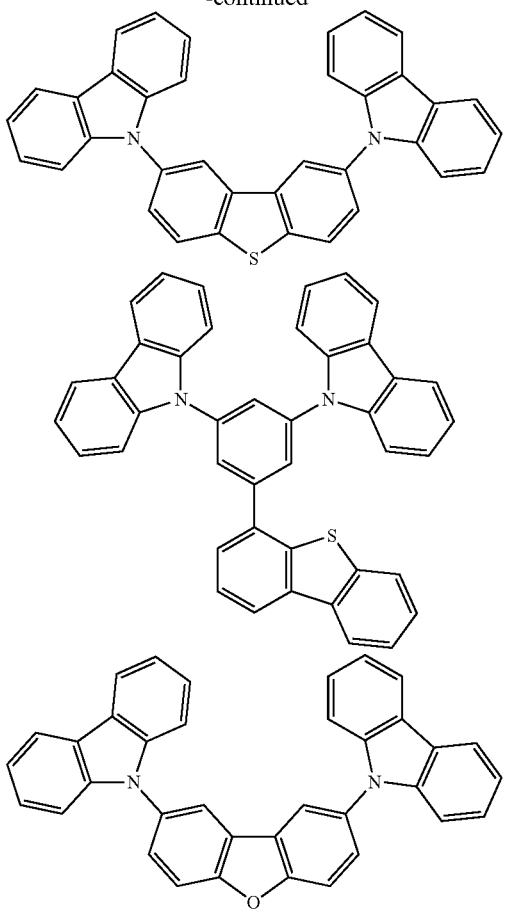

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. The hole injection material can be present in the liquid medium in an amount from 0.5 to 10 percent by weight. The hole injection layer can be applied by any continuous or discontinuous liquid deposition technique. In one embodiment, the hole injection layer is applied by spin coating. In one embodiment, the hole injection layer is applied by ink jet printing. In one embodiment, the hole injection layer is applied by continuous nozzle printing. In one embodiment, the hole injection layer is applied by slot-die coating. After liquid deposition, the liquid medium can be removed in air, in an inert atmosphere, or by vacuum, at room temperature or with heating.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In one embodiment, the hole transport layer is applied by spin coating. In one embodiment, the hole transport layer is applied by ink jet printing. In one embodiment, the hole transport layer is applied by continuous nozzle printing. In one embodiment, the hole transport layer is applied by slot-die coating. After liquid deposition, the liquid medium can be removed in air, in an inert atmosphere, or by vacuum, at room temperature or with heating.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. In one embodiment, the photoactive layer is applied by continuous nozzle printing. In one embodiment, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In one embodiment, it is deposited by thermal evaporation under vacuum.

The electron injection layer can be deposited by any vapor deposition method. In one embodiment, it is deposited by thermal evaporation under vacuum.

The cathode can be deposited by any vapor deposition method. In one embodiment, it is deposited by thermal evaporation under vacuum.

EXAMPLES

The concepts described herein will be further described in the following examples, which do not limit the scope of the invention described in the claims.

Synthesis Example 1

This example illustrates the synthesis of Compound L1 and Compound B1.

The synthesis was carried out in two steps as follows:

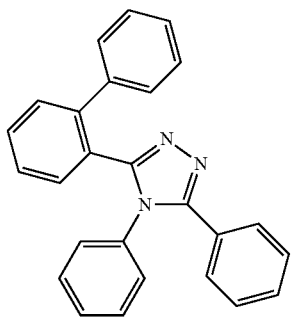 [SMILES: c1ccc(-c2ccccc2-c2nnc(-c3ccccc3)n2-c2ccccc2)cc1]

Step 1: Synthesis of 3-([1,1'-biphenyl]-2-yl)-4,5-diphenyl-4H-1,2,4-triazole, Compound L1

A 50 mL round bottom flask containing a stir bar was charged with aniline (2.27 g, 24.4 mmol) under nitrogen. The aniline was stirred and treated with anhydrous aluminum chloride (0.91 g, 6.8 mmol) in small portions to afford a suspension. The mixture was stirred under nitrogen and heated to 138-140° C. to afford a yellow solution. The mixture was stirred and maintained at 138-140° C. for 2 h. The mixture was cooled to room temperature and treated with 2-([1,1'-biphenyl]-2-yl)-5-phenyl-1,3,4-oxadiazole (see procedure from Example 1, 2.70 g, 9.05 mmol) followed by anhydrous 1-methyl-2-pyrrolidinone (2.70 mL). The mixture was then heated at reflux for 19 h. The mixture was cooled to room temperature, triturated with 60 mL of 15% aqueous HCl, and the hard solid scraped and broken up with a spatula. The mixture was extracted five times with ethyl acetate. The ethyl acetate layers were combined, washed three times with brine, dried over MgSO$_4$, filtered, concentrated, and dried under high vacuum at room temperature to a viscous oil. The oil was chromatographed on a Biotage® 340 g silica gel column using a gradient of 12% to 100% ethyl acetate in hexane. Fractions containing the component of the major peak were combined and concentrated to afford 3.06 g of the desired product as a viscous, pale yellow foam which crystallized upon standing to an off-white solid (91% yield). $^1$HNMR (CD$_2$Cl$_2$) δ 7.77 (d, 1H), 7.53 (mult, 2H), 7.29 (mult, 6H), 7.15 (mult, 4H), 6.99 (t, 2H), 6.83 (d, 2H), 6.21 (d, 2H).

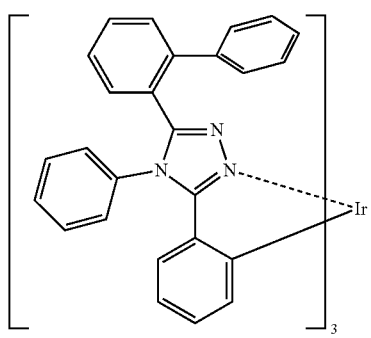

Step 2: Synthesis of Fac-tris-(2-(5-([1,1'-biphenyl]-2-yl)-4-phenyl-4H-1,2,4-triazol-3-yl)phenyl)iridium (III), Compound B1

A 6.5 mL pressure reactor was charged with the ligand 3-([1,1'-biphenyl]-2-yl)-4,5-diphenyl-4H-1,2,4-triazole (2.30 g, 6.16 mmol) and iridium tris-acetylacetonate (0.92 g, 1.87 g) and sealed under nitrogen. The mixture was heated to an internal temperature of 245° C. and the temperature maintained at 245° C. for 60 h. The mixture was then cooled to room temperature. The crude product was triturated with ethyl acetate and transferred to a 500 mL flask. It was concentrated to afford 3.08 g of a dark solid. The solid was triturated with ethyl acetate and the undissolved solid was filtered off, washed with small portions of ethyl acetate, and air dried to afford 0.94 g of a green solid. This was dissolved/suspended in ~60 mL of chloroform. Most of the solid dissolved but some suspension remained. The mixture was chromatographed on a 100 g Biotage® silica gel column eluted with 50% ethyl acetate in chloroform. Fractions containing product were combined and concentrated to afford 0.14 g of a yellow solid. This was suspended in small portions of chloroform and transferred to an amber vial. The solution was concentrated under a slow stream of nitrogen to a yellow solid. This was dissolved in 50 mL of chloroform at room temperature under nitrogen. The slightly cloudy solution was filtered through a medium frit funnel to afford a clear solution. The filtrate was concentrated to a volume of about 15 mL. The solution was treated in portions with about 30 mL of pentane forming a fine yellow solid. The solid was filtered off, washed three times with pentane, and briefly air dried to afford 0.105 g of a yellow solid which was used for device testing. UPLC-MS indicated a purity of ~94%. $^1$HNMR (CDCl$_3$) δ 7.90 (br s, 1H), 7.42 (mult, 2H), 7.30-6.60 (mult, 1H), 6.58 (br t, 2H), 6.38 (br d, 2H), 6.20 (br, 1H).

Synthesis Example 2

This example illustrates the synthesis of Compound L2 and Compound B2.

The synthesis was carried out in two steps as follows:

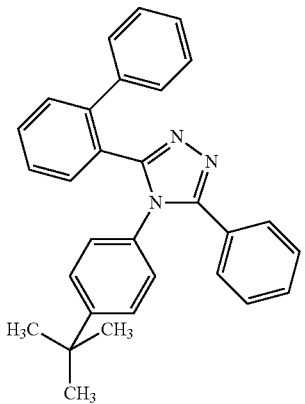 [SMILES: CC(C)(C)c1ccc(-n2c(-c3ccccc3)nnc2-c2ccccc2-c2ccccc2)cc1]

Step 1: Synthesis of 3-([1,1'-biphenyl]-2-yl)-4-(4-(tert-butyl)phenyl)-5-phenyl-4H-1,2,4-triazole, Compound L2

In a nitrogen-filled glove box, 4-t-butylaniline (3.48 g, 23.3 mmol) was added to a 100 mL 3-neck flask containing a stirbar. To this was added anhydrous aluminum chloride (0.87 g, 6.50 mmol) in small portions to afford a brown solid. The mixture was stirred under nitrogen and heated slowly to 138-140° C. to afford a dark solution. The mixture was stirred and maintained at 138-140° C. for 2 h. The mixture remained dark during the heating period. The mixture was kept under nitrogen and treated with 2-([1,1'-biphenyl]-2-yl)-5-phenyl-1,3,4-oxadiazole (see procedure from Example 1, 2.58 g, 8.65 mmol) followed by anhydrous 1-methyl-2-pyrrolidinone (2.6 mL). The mixture was then heated to reflux. The mixture was heated at reflux for 19 h under nitrogen and then cooled to room temperature under nitrogen forming a dark mass. This was triturated with 55 mL of 10% aqueous HCl at room temperature. The resulting hard solid was broken up with a spatula. The mixture was extracted with ethyl acetate several times. The combined ethyl acetate extracts were washed once with water, washed with aqueous $Na_2CO_3$, dried over $MgSO_4$, filtered and concentrated to afford 6.31 g of a dark oil. The dark oil was chromatographed on a Biotage® 340 g silica gel column using a gradient of 12% to 100% ethyl acetate in hexane. Fractions containing the major product were combined and concentrated to afford 3.41 g of the desired product as an off-white glass (92% yield). $^1$HNMR ($CD_2Cl_2$) δ 7.79 (mult, 1H), 7.54 (mult, 2H), 7.30 (mult, 6H), 7.17 (mult, 1H), 7.11 (t, 2H), 6.98 (d, 2H), 6.78 (d, 2H), 6.11 (d, 2H), 1.25 (s, 9H).

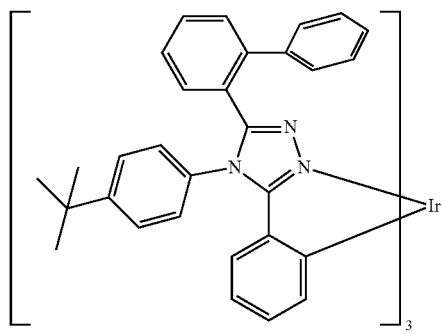

Step 2: Synthesis of Fac-tris-(2-(5-([1,1'-biphenyl]-2-yl)-4-(4-(tert-butyl)phenyl)-4H-1,2,4-triazol-3yl) phenyl)iridium(III), Compound B2

The triazole ligand 3-([1,1'-biphenyl]-2-yl)-4-(4-(tert-butyl)phenyl)-5-phenyl-4H-1,2,4-triazole (2.38 g, 5.54 mmol) and Ir(acac)$_3$ (0.83 g, 1.70 mmol) were premixed in a 5 dram vial under nitrogen in a glove box. The mixture was transferred to a 6.5 mL stainless steel pressure vessel, and the vessel sealed tightly under nitrogen. The pressure vessel was then heated to an internal temperature of 249° C. The mixture was heated for 55 h and then allowed to slowly cool to room temperature. The reaction mixture was triturated with ethyl acetate and transferred to a 500 mL round bottom flask. The dark suspension was concentrated to afford 3.40 g of a dark glass. The dark glass was chromatographed on a Biotage® 340 g silica gel column using a gradient of 20% to 50% ethyl acetate in hexane. The total amount of product obtained after chromatography was 1.56 g (62% yield). $^1$HNMR ($CD_2Cl_2$) δ 7.92 (br d, 1H), 7.60-5.90 (broad overlapping multiplets, 16H), 1.29 (s, 9H). UPLC-MS indicated a purity of 99.6%.

Synthesis Example 3

This example illustrates the synthesis of Compound L5 and Compound B5.

The synthesis was carried out in two steps as follows:

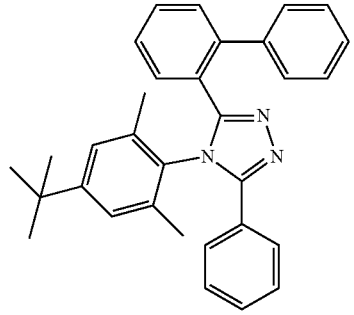 [SMILES: Cc1cc(C(C)(C)C)cc(C)c1-n1c(-c2ccccc2)nnc1-c1ccccc1-c1ccccc1]

Step 1: Synthesis of 3-([1,1'-biphenyl]-2-yl)-4-(4-(tert-butyl)-2,6-dimethylphenyl)-5-phenyl-4H-1,2,4-triazole, Compound L5

Under nitrogen, a 250 mL 3-neck flask containing a stirbar was charged with 4-tert-butyl-2,6-dimethylaniline (Maybridge Chemical, 13.0 g, 73.6 mmol). The 2,6-dimethylaniline was stirred and treated with anhydrous aluminum chloride (2.45 g, 18.4 mmol) in small portions. The resulting solution was stirred under nitrogen and heated at 138-140° C. for 2.5 h to afford a red-purple solution. The mixture was kept under nitrogen and treated with 2-([1,1'-biphenyl]-2-yl)-5-phenyl-1,3,4-oxadiazole (see procedure in Example 1, 3.01 g, 10.1 mmol) followed by anhydrous 1-methyl-2-pyrrolidinone (3.0 mL). The mixture was heated at reflux for a total of 22 h and then cooled to room temperature, affording a dark solid. This was treated with 100 mL of 10% aqueous HCl at room temperature to afford a suspension. The mixture was extracted several times with ethyl acetate, and the extracts were combined and dried over $Na_2SO_4$. The mixture was filtered and the filtrate was concentrated to afford an oil. The oil was chromatographed on a Biotage® 340 g silica gel column using a gradient of 12% to 100% ethyl acetate in hexane. Fractions containing product were combined and concentrated to afford an off-white solid. This was dried under high vacuum at room temperature to afford 3.37 g (73% yield) of the desired product as an off white solid. ¹HNMR (CD₂Cl₂) δ 7.47 (mult, 2H), 7.37 (t, 1H), 7.32 (mult, 3H), 7.25 (mult, 6H), 7.12 (mult 2H), 6.87 (s, 2H), 1.40 (s, 6H), 1.28 (s, 9H).

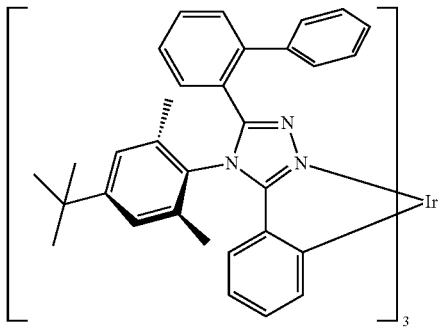

Step 2: Synthesis of Fac-tris-(2-(5-([1,1'-biphenyl]-2-yl)-4-(4-(tert-butyl)-2,6-dimethylphenyl)-4H-1,2,4-triazol-3-yl)phenyl)iridium(III), Compound B5

A 10 mL stainless steel pressure vessel under nitrogen was charged with a mixture of the ligand 3-([1,1'-biphenyl]-2-yl)-4-(4-(tert-butyl)-2,6-dimethylphenyl)-5-phenyl-4H-1,2,4-triazole (1.68 g, 3.67 mmol) and iridium tris-acetylacetonate (0.55 g, 1.1 mmol). The vessel was sealed tightly while under nitrogen. The vessel was then heated over a ~1 h period to an internal temperature of 248° C. The mixture was heated at 248° C. for 60 h. The mixture was cooled to room temperature to leave a dark solid. It was triturated several times with ethyl acetate and transferred to a 500 mL flask. The mixture was concentrated to afford 2.18 g of a dark glass. The glass was chromatographed on a Biotage® 340 g silica gel column using a gradient of 6% to 50% ethyl acetate in hexane. Fractions containing product were combined and concentrated to afford 1.00 g of a yellow glass. This was suspended in warm hexane but little of the compound dissolved. Toluene was added dropwise and the mixture was kept warm. The solid slowly dissolved to afford a yellow solution which was allowed to cool to room temperature and stand overnight as a yellow solid formed. The yellow solid was filtered off, washed once with minimal toluene/hexane (1:1), washed twice with hexane, and dried under high vacuum at room temperature to afford 0.55 g of the desired product as a yellow solid. ¹HNMR (CD₂Cl₂) δ 7.64 (d, 1H), 7.53 (t, 1H), 7.40 (t, 1H), 7.28 (d, 1H), 7.10 (br mult, 2H), 6.92 (s, 2H), 6.81 (mult, 4H), 6.67 (t, 1H), 6.54 (t, 1H), 6.20 (d, 1H), 1.55 (br s, 3H), 1.30 (s, 12H). UPLC-MS indicated a purity of 99.4%.

Synthesis Example 4

This example illustrates the synthesis of Compound L10 and Compound B10.

The synthesis was carried out in three steps as follows:

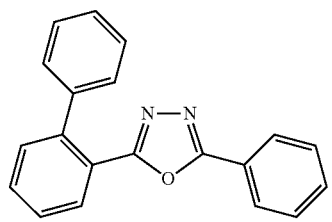 [SMILES: c1ccc(-c2nnc(-c3ccccc3-c3ccccc3)o2)cc1]

Step 1: Synthesis of 2-([1,1'-biphenyl]-2-yl)-5-phenyl-1,3,4-oxadiazole 2-biphenylcarboxylic acid (15.0 g, 75.7 mmol) was dissolved in 700 mL of anhydrous THF under nitrogen. The solution was treated with diisopropylethylamine (29.4 g, 227 mmol, 3.0 equiv) followed by 2-(7-Aza-1H-benzotriazole-1-yl)-1,1,3,3-tetramethyluronium hexafluorophosphate ("HATU," 31.7 g, 83.2 mmol) and benzoyl hydrazine (10.3 g, 75.7 mmol). The mixture was stirred under nitrogen at room temperature for 2.5 h and then treated with additional diisopropylethylamine (151 mmol, 2.0 equiv) followed by p-tosyl chloride (227 mmol, 3.0 equiv), added in portions. The mixture was stirred at room temperature under nitrogen overnight. The mixture was then treated slowly with 21 mL of 29% aqueous ammonium hydroxide. A light yellow precipitate formed after a few min. The solid was filtered off and washed with acetonitrile. The filtrate was concentrated to afford a syrup. This was suspended in 600 mL of water and extracted twice with dichloromethane. The dichloromethane extracts were combined, washed once with 500 mL of water, dried over Na₂SO₄, filtered, and concentrated to afford a sludge. The sludge was redissolved in dichloromethane and washed 5 times with 500 mL portions of water. The dichloromethane layer was dried over MgSO₄, filtered, and concentrated to afford a tacky solid. The solid was chromatographed on a Biotage® 340 g silica gel column using a gradient of 5% to 40% ethyl acetate in hexane. The product-containing fractions were combined and concentrated to afford a viscous pale yellow oil (10.3 g, 91% yield). ¹HNMR (CD₂Cl₂) δ 8.17 (d, 1H), 7.65 (mult, 3H), 7.56 (dt, 1H), 7.50 (mult, 2H), 7.43 (mult, 5H), 7.34 (mult, 2H).

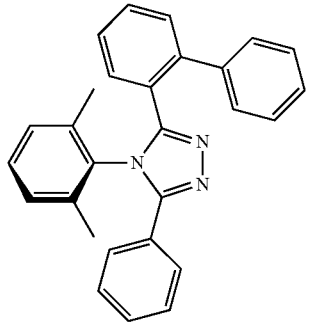

Step 2: Synthesis of 3-([1,1'-biphenyl]-2-yl)-4-(2,6-dimethylphenyl)-5-phenyl-4H-1,2,4-triazole, Compound L10

Reference: C. I. Chiriac et al, Rev. Roum. Chim., 2010, 55(3), 175-177. A 100 mL round bottom flask containing a stir bar was charged with 2,6-dimethylaniline (5.50 g, 16.8 mmol) under nitrogen. The 2,6-dimethylaniline was stirred and treated with 0.25 equiv of anhydrous aluminum chloride in small portions to afford a yellow suspension. The mixture was stirred under nitrogen and heated to 138-140° C. to afford a deep red-purple solution. The mixture was stirred and maintained at 138-140° C. for 2 h. The mixture was kept under nitrogen and treated with 2-([1,1'-biphenyl]-2-yl)-5-phenyl-1,3,4-oxadiazole (5.00 g, 0.37 equiv) followed by anhydrous 1-methyl-2-pyrrolidinone (5.0 mL). The mixture was then heated to reflux. The mixture was a dark purple liquid after 67 h at reflux. The mixture was cooled to room temperature forming a solid mass. It was triturated with 40 mL of 15% aqueous HCl and the hard solid was scraped and broken up with a spatula. The mixture was stirred for 2 h at room temperature while scraping the hard glass with a spatula. The mixture was a suspension containing a relatively small amount of fine white solid which passed through a medium frit funnel. The entire mixture was extracted 5 times with ethyl acetate. The ethyl acetate extracts were combined, washed twice with brine, dried over MgSO4, filtered, and concentrated to afford an oil. The oil was chromatographed on a Biotage® 340 g silica gel column using a gradient of 12% to 100% ethyl acetate in hexane. Fractions containing the component of the major peak were combined and concentrated to afford 6.31 g (94% yield) of a pale yellow oil which crystallized upon standing. $^1$HNMR (CD$_2$Cl$_2$) δ 7.47 (mult, 2H), 7.37-7.13 (overlapping multiplets, 13H), 6.88 (d, 2H), 1.43 (s, 6H).

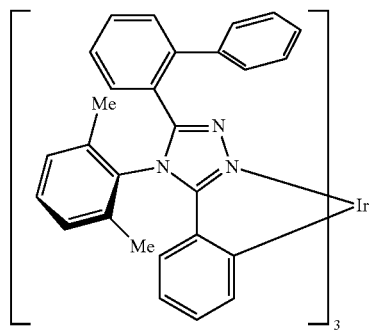

Step 3: Synthesis of Fac-tris-(2-(5-([1,1'-biphenyl]-2-yl)-4-(2,6-dimethylphenyl)-4H-1,2,4-triazol-3-yl)phenyl)iridium(III), Compound B10

In a nitrogen-filled glove box, the ligand 3-([1,1'-biphenyl]-2-yl)-4-(2,6-dimethylphenyl)-5-phenyl-4H-1,2,4-triazole (2.52 g, 6.28 mmol) and Ir(acac)$_3$ (0.93 g, 1.90 mmol) were placed in a 6.5 mL capacity stainless steel pressure reactor. The vessel was sealed tightly under nitrogen. The pressure vessel was heated over a one hour period to an internal reaction mixture temperature of 290° C. The internal reaction temperature was maintained at 287-288° C. for a total of 42.5 h; the reaction mixture was then allowed to cool to room temperature. The reaction mixture residue was broken up and transferred with multiple portions of ethyl acetate (~200 mL total) to a 500 mL pear shaped flask. The mixture was concentrated to afford a yellow-brown glass. This was chromatographed on a Biotage® 340 g silica gel column using a gradient of 8% to 66% ethyl acetate in hexane. This afforded 1.35 g of a yellow glass. Recrystallization from toluene/hexane afforded 1.10 g of a yellow solid. This material was chromatographed a second time on a Biotage® 100 g silica gel column using a gradient of 8% to 66% ethyl acetate in hexane. The major fractions of the peak centered at 9 column volumes were not combined but were concentrated individually to afford 0.163 g of a yellow glass (fraction A), 0.464 g of a yellow glass (fraction B), 0.305 g of a yellow glass (fraction C), and 0.095 g of a yellow glass (faction D). The total recovery was 1.03 g. UPLC/Mass Spectral Analysis of fraction B indicated a purity of 99.0%, and this material was used for device testing. $^1$HNMR (CD$_2$Cl$_2$) δ 7.64 (d, 1H), 7.52 (t, 1H), 7.38 (t, 1H), 7.30 (d, 1H), 7.16 (mult, 3H), 6.94 (mult 2H), 6.80 (mult, 4H), 6.65 (t, 1H), 6.54 (t, 1H), 6.20 (d, 1H), 1.63 (br, 3H), 1.29 (br, 3H).

Synthesis Example 5

This example illustrates the synthesis of Compound L3 and Compound B3.

The synthesis is carried out in six steps.

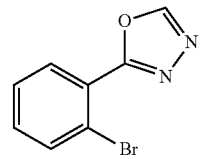 [SMILES: Brc1ccccc1-c1nnco1]

Step 1. 2-(2-Bromophenyl)-1,3,4-oxadiazole

2-Bromobenzohydrazide (5.0 g, 23 mmol) and triethyl orthoformate (20 mL) were charged into a 200-mL two-necked round-bottom flask, and the mixture was vigorously stirred at 160° C. for 15 h. The solvent was evaporated under reduced pressure (300 mTorr). The resulting brow liquid mixture was then dissolved in dichloromethane and washed with 1N HCl (1×50 mL) then brine (1×50 mL). The organic layer was dried over MgSO$_4$ and concentrated under reduced pressure. Biotage® purification was performed to afford a light yellow oil (4.0 g, 75%). $^1$H NMR (500 MHz, CD$_2$Cl$_2$) δ 8.56 (m, 1H, triazole-H), 7.89 (dd, J=1.7, 7.8 Hz, 1H, C6-H), 7.67 (dd, J=1.1, 8.0 Hz, 1H, C3-H), 7.48 (dt, J=1.2, 7.6 Hz, 1H, C4-H), 7.41 (dt, J=1.7, 7.8 Hz, 1H, C5-H).

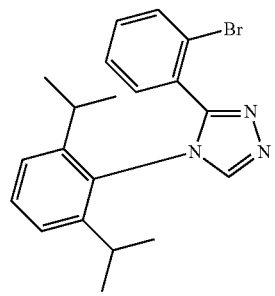 [SMILES: CC(C)c1cccc(C(C)C)c1-n1cnnc1-c1ccccc1Br]

Step 2. 3-(2-Bromo-phenyl)-4-(2,6-diisopropyl-phenyl)-4H-[1,2,4]triazole 2-(2-Bromo-phenyl)-[1,3,4]oxadiazole (4.15 g, 18.4 mmol), 2,6-diisopropylaniline (2.27 g, 12.8 mmol), and o-dichlorobenzene (10 mL) in a 100-ml round-bottom flask equipped with a stir bar, condenser and N$_2$ bubbler. Trifluoroacetic acid (1.4 mL, 18 mmol) was added. The reaction mixture was stirred above a heating block set at 185° C. for 17 h. The reaction mixture was then allowed to cool to room temperature and poured into water. Aqueous 10% Na$_2$CO$_3$ was added to pH ~9. The product was extracted with ethyl acetate. The organic layers were washed with brine, dried over MgSO$_4$, and concentrated under reduced pressure to give a blueish-green liquid (18 g). o-Dichlorobenzene was removed by vacuum at 85° C. to give a blueish-green solid. Purification of this crude product was performed with Biotage® to give a colorless solid (3.2 g, 65%). ¹H NMR (500 MHz, CD₂Cl₂) δ 8.20 (s, 1H, triazole-H), 7.68 (dd, J=1.2, 8.1 Hz, 1H, ArH), 7.39 (t, J=7.8 Hz, 1H, ArH), 7.23-7.18 (m, 3H, ArH), 7.14 (dt, J=1.2, 7.8 Hz, 1H, ArH), 6.92 (dd, J=1.7, 7.7 Hz, 1H, ArH), 2.48 (sept, J=6.8 Hz, 2H, CH(CH₃)₂), 1.09 (d, J=6.8 Hz, 6H, CH(CH₃)₂), 1.00 (d, J=6.8 Hz, 6H, CH(CH₃)₂).

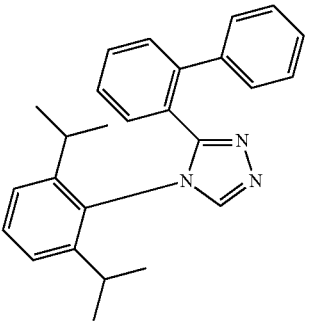 [SMILES: CC(C)c1cccc(C(C)C)c1-n1cnnc1-c1ccccc1-c1ccccc1]

Step 3. 3-Biphenyl-2-yl-4-(2,6-diisopropyl-phenyl-4H-[1,2,4]triazole

To a 250 ml, 2-neck round bottom flask equipped with a stir bar, condenser, N₂ bubbler and N₂ sparge tube were charged with 3-(2-bromo-phenyl)-4-(2,6-diisopropyl-phenyl)-4H-[1,2,4]triazole (3.2 g, 8.3 mmol), toluene (75 mL), phenylboronic acid (2.03 g, 16.6 mmol), and K₃PO₄ monohydrate (5.75 g, 25.0 mmol). The mixture was sparged with N₂ for 45 min. In a glove box, a solution of Pd₂dba₃ (0.23 g, 0.25 mmol) and S-Phos (0.41 g, 1.0 mmol) in toluene (50 mL) was prepared in a sealed round bottom flask. The mixture was stirred at room temperature for 20 min and then cannula transferred to the reaction flask. The reaction mixture was stirred with the heating block set to 140° C. for 17 h. The reaction mixture was diluted with dichloromethane (100 mL) and passed through a plug of Celite® on top of silica. Ethyl acetate (250 mL) was passed through the plug. The filtrate was concentrated under reduced pressure and the crude product was purified by Biotage® to give a white powder (3.0 g, 95%). ¹H NMR (500 MHz, CD₂Cl₂) δ 8.04 (s, 1H, triazole-H), 7.44-7.31 (m, 8H, ArH), 7.23-7.21 (m, 2H, ArH), 7.12 (m, 1H, ArH), 6.93 (m, 1H, ArH), 2.32 (sept, J=6.8 Hz, 2H, CH(CH₃)₂), 1.03 (d, J=6.8 Hz, 6H, CH(CH₃)₂), 0.97 (d, J=6.8 Hz, 6H, CH(CH₃)₂).

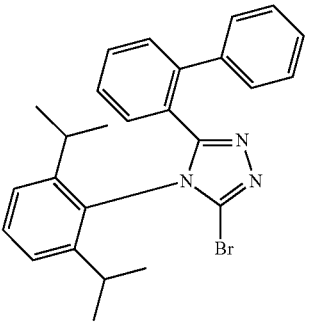 [SMILES: CC(C)c1cccc(C(C)C)c1-n1c(Br)nnc1-c1ccccc1-c1ccccc1]

Step 4. 3-Biphenyl-2-yl-5-bromo-4-(2,6-diisopropyl-phenyl)-4H-[1,2,4]triazole

To a 100-ml round bottom flask equipped with a stir bar, reflux condenser and N₂ bubbler were added 3-biphenyl-2-yl-4-(2,6-diisopropyl-phenyl-4H-[1,2,4]triazole (3.0 g, 7.9 mmol), carbon tetrachloride (20 mL), acetic acid (20 mL), then N-bromosuccinimide (1.8, 9.8 mmol). The reaction mixture was heated with an aluminum block set at 120° C. After 5 h, analysis by TLC indicated almost complete conversion of starting materials. The mixture was allowed to cool to room temperature. Aqueous 10% sodium carbonate was added to pH ~8-9. The crude product was extracted with dichloromethane and washed with brine. The organic layer was separated and dried over MgSO₄, filtered and concentrated on rotary evaporator and dried under high vacuum. Purification by Biotage® automated flash column chromatography afforded a white powder (1.9 g, 52%). ¹H NMR (500 MHz, CD₂Cl₂) δ 7.51 (t, J=7.8 Hz, 1H, ArH), 7.39-7.28 (m, 9H, ArH), 7.09 (m, 1H, ArH), 6.95 (m, 1H, ArH), 2.35 (sept, J=6.8 Hz, 2H, CH(CH₃)₂), 1.16 (d, J=6.7 Hz, 6H, CH(CH₃)₂), 0.97 (d, J=6.8 Hz, 6H, CH(CH₃)₂).

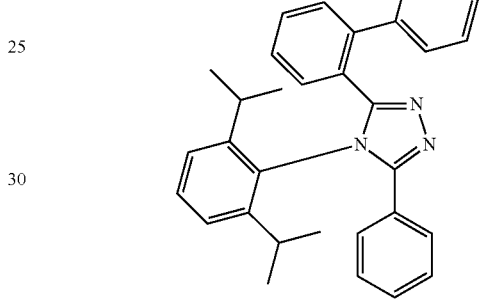

Step 5. 3-Biphenyl-2-yl-4-(2,6-diisopropyl-pheny)-5-phenyl-4H-[1,2,4]triazole, Compound L3

To a 250 ml, 2-neck round bottom flask equipped with a stir bar, condenser, N₂ bubbler and N₂ sparge tube were charged 3-biphenyl-2-yl-5-bromo-4-(2,6-diisopropyl-phenyl)-4H-[1,2,4]triazole (1.9 g, 4.1 mmol), phenylboronic acid (1.0 g, 8.2 mmol), degassed toluene (50 mL) and K₃PO₄ monohydrate (2.9 g, 12 mmol). The mixture was sparged with N₂ for 40 min. In a glove box, a solution of Pd₂dba₃ (0.11 g, 0.12 mmol) and S-Phos (0.20 g, 0.49 mmol) in toluene (20 mL) was prepared in a sealed round bottom flask. The mixture was stirred at room temperature for 20 min and then cannula transferred to the reaction flask. The reaction mixture was stirred with the heating block set to 140° C. for 2.5 h. After the mixture was cooled to room temperature, it was diluted with dichloromethane and passed through a plug of Celite® on top of silica. Ethyl acetate was used in to rinse the product from the plug. The filtrate was concentrated under reduced pressure. Biotage® purification was performed to give a white powder (1.65 g, 88%). ¹H NMR (500 MHz, CD₂Cl₂) δ 7.50 (t, J=7.8 Hz, 1H, ArH), 7.42-7.20 (m, 14H, ArH), 7.05 (m, 1H, ArH), 6.81 (dd, J=1.0, 7.9 Hz, 1H, ArH), 2.47 (sept, J=6.8 Hz, 2H, CH(CH₃)₂), 0.85 (d, J=6.8 Hz, 6H, CH(CH₃)₂), 0.74 (d, J=6.8 Hz, 6H, CH(CH₃)₂).

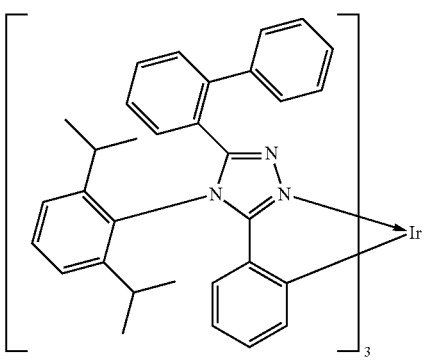

Step 6. Tris(2-{5-(biphenyl-2-yl)-4-[2,6-di(propan-2-yl)phenyl]-4H-1,2,4-triazol-3-yl-κN²}phenyl-κC¹) iridium, Compound B3

Into a 20-ml scintillation vial, were added 3-biphenyl-2-yl-4-(2,6-diisopropyl-pheny)-5-phenyl-4H-[1,2,4]triazole (1.6 g, 3.5 mmol) and iridium acetylacetonate (0.52 g, 1.1 mmol) and mixed. The mixture was transferred to a 6-mL stainless steel pressure tube, which was brought into the glove box and sealed. The tube was heated at 250° C. for 65 h. After being cooled to room temperature, the crude product was rinsed from tube with CH$_2$Cl$_2$ and was purified on Biotage® chromatography followed by recrystallization from boiling toluene. The hot toluene solution was poured into MeOH (200 mL). A yellow powder was isolated by filtering through a fritted funnel and rinsing with MeOH and dried under reduced pressure to give (1.1 g, 66%). ¹H NMR (500 MHz, CD$_2$Cl$_2$) δ 7.57 (dd, J=1.0, 7.9 Hz, 3H, ArH), 7.53 (d, J=7.3 Hz, 6H, ArH), 7.48 (dt, J=1.3, 7.6 Hz, 3H, ArH), 7.41 (t, J=7.8 Hz, 3H, ArH), 7.19-7.17 (m, 12H, ArH), 6.88 (t, J=7.8 Hz, 6H, ArH), 6.74-6.70 (m, 6H, ArH), 6.60 (dt, J=1.3, 7.4 Hz, 3H, ArH), 6.45 (m, 3H, ArH), 5.97 (d, J=7.2 Hz, 3H, ArH), 2.53 (septet, J=6.7 Hz, 3H, CH(CH$_3$)$_2$), 1.83 (septet, J=6.7 Hz, 3H, CH(CH$_3$)$_2$), 0.71-0.67 (m, 27H, CH(CH$_3$)$_2$), 0.61 (d, J=6.6 Hz, 9H, CH(CH$_3$)$_2$). LC/MS (SQ with ESI) C$_{96}$H$_{90}$IrN$_9$ calcd: 1562.77 ([M+H]+). Found: 1562.39.

Synthesis Example 6

This example illustrates the synthesis of Compound L4 and Compound B4.

The synthesis was carried out in three steps.

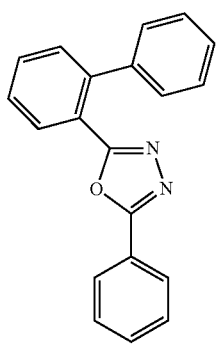 [SMILES: c1ccc(-c2nnc(-c3ccccc3-c3ccccc3)o2)cc1]

Step 1. 2-(Biphenyl-2-yl)-5-phenyl-1,3,4-oxadiazole

To a solution of biphenylcarboxylic acid (5.00 g, 25.22 mmol) in (CH$_2$Cl$_2$, 50 mL) at −5° C., was added a catalytic amount of anhydrous DMF (3 drops). This was followed by the dropwise addition of oxalyl chloride (3.2 mL, 38 mmol) in CH$_2$Cl$_2$ (12.5 mL). The reaction was allowed to warm to ambient temperature and stirred for 16 h. The reaction mixture was concentrated under reduced pressure to about ~5.8 g of acid chloride, which was used immediately without further characterization. In the fume hood, 5-phenyl-1H-tetrazole (3.4 g, 23 mmol) was added to an oven dried 250 mL 2-neck RBF containing a magnetic stir bar, followed by VERY CAREFUL addition of the acid chloride then pyridine (30 mL). The reaction mixture was stirred at 90° C. for when GC/MS analysis was performed to show clean formation of desired product from almost full conversion. The reaction mixture was transferred to a 1-neck tear-drop flask with the aid of toluene (30 mL). The mixture was concentrated under reduced pressure. Biotage® purification was performed to yield a colorless solid (5 g, 72%). ¹H NMR (500 MHz, CD$_2$Cl$_2$, reference peak: CH$_2$Cl$_2$ δ 5.30) δ 8.13 (m, 1H, ArH), 7.63-7.59 (m, 3H, ArH), 7.53 (dt, J=1.4, 7.6 Hz, 1H, ArH), 7.49-7.45 (m, 2H, ArH), 7.41-7.37 (m, 5H, ArH), 7.33-7.29 (m, 2H, ArH).

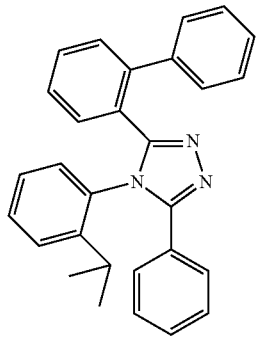 [SMILES: CC(C)c1ccccc1-n1c(-c2ccccc2)nnc1-c1ccccc1-c1ccccc1]

Step 2. 3-(Biphenyl-2-yl)-5-phenyl-4-[2-(propan-2-yl)phenyl]-4H-1,2,4-triazole, Compound L4

Inside the glovebox, 2-isopropylaniline (1.88 g, 13.9 mmol) was added to a 25-ml Schlenk tube containing a stir bar. It was stirred and treated with anhydrous aluminum chloride (0.46 g, 3.4 g) in small portions with stirring to give a light tan solution. The mixture was stirred at 140° C. for 1 h. The mixture became deeper red during the heating period. The mixture was treated with 2-(biphenyl-2-yl)-5-phenyl-1,3,4-oxadiazole (1.6 g, 5.4 mmol) followed by anhydrous NMP (1.5 mL) and heated at 210° C. for 40 h. The reaction was quenched by water (15 mL) and the product was extract with ethyl acetate (2×50 mL). Biotage® purification was performed to afford a white powder (1.1 g, 49%). ¹H NMR (500 MHz, CD$_2$Cl$_2$) δ 7.61 (dd, J=1.1, 7.6 Hz, 1H, ArH), 7.47 (dt, J=1.3, 7.6 Hz, 1H, ArH), 7.40 (dt, J=1.2, 7.6 Hz, 1H, ArH), 7.32 (dd, J=0.9, 7.7 Hz, 1H, ArH), 7.29-7.24 (m, 6H, ArH), 7.21-7.16 (m, 3H, ArH), 7.11 (dd, J=1.1, 7.8 Hz, 1H, ArH), 7.07-7.05 (m, 2H, ArH), 6.70 (J=1.2, 7.6 Hz, 1H, ArH), 5.58 (dd, J=1.0, 7.9 Hz, 1H, ArH), 2.35 (sept, J=6.8 Hz, 1H, ArCH(CH$_3$)$_2$), 0.71 (d, J=6.8 Hz, 3H, ArCH(CH$_3$)$_2$), 0.64 (d, J=6.8 Hz, 3H, ArCH(CH$_3$)$_2$).

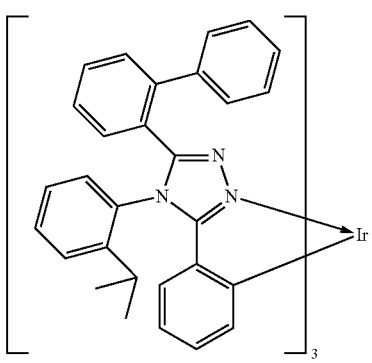

Step 3. Tris(2-{5-(biphenyl-2-yl)-4-[2-(propan-2-yl)phenyl]-4H-1,2,4-triazol-3-yl-κN²}phenyl-κC¹)iridium, Compound B4

3-(Biphenyl-2-yl)-5-phenyl-4-[2-(propan-2-yl)phenyl]-4H-1,2,4-triazole (0.81 g, 1.9 mmol) and iridium acetylacetonate (0.29 g, 0.59 mmol) were combined into a 20-mL scintillation vial and charged into a 6-mL stainless steel tube. The tube was brought into the glovebox and sealed. The mixture was heated at 250° C. for 95 h. The crude material was purified by Biotage to afford separate diastereomers. One of these diastereomers (0.078 g) was submitted for device testing. $^1$H NMR (500 MHz, CD$_2$Cl$_2$) δ 7.95 (d, J=7.8 Hz, 1H, ArH), 7.80 (m, 1H, ArH), 7.54 (m, 1H, ArH), 7.50-7.46 (m, 2H, ArH), 7.45-7.39 (m, 3H, ArH), 7.34-7.17 (m, 18H, ArH), 7.00 (b, 1H, ArH), 6.89-6.80 (m, 4H, ArH), 6.79-6.66 (m, 6H, ArH), 6.62-6.52 (m, 6H, ArH), 6.45-6.40 (m, 2H, ArH), 6.02 (t, J=8.0 Hz, 2H, ArH), 5.95 (d, J=7.7 Hz, 1H, ArH), 5.80 (d, J=7.5 Hz, 1H, ArH), 5.58 (b, 1H, ArH), 5.44 (b, 1H, ArH), 2.84 (m, 1H, ArCH(CH$_3$)$_2$), 2.41 (m, 1H, ArCH(CH$_3$)$_2$), 2.15 (p, J=6.8 Hz, 1H, ArCH(CH$_3$)$_2$), 0.97 (d, J=6.7 Hz, 3H, ArCH(CH$_3$)$_2$), 0.89 (d, J=7.0 Hz, 3H, ArCH(CH$_3$)$_2$), 0.78 (t, J=7.2 Hz, 3H, ArCH(CH$_3$)$_2$), 0.65 (d, J=6.7 Hz, 3H, ArCH(CH$_3$)$_2$), 0.62 (d, J=6.7 Hz, 3H, ArCH(CH$_3$)$_2$). LC/MS (SQ with ESI) C$_{87}$H$_{72}$IrN$_9$ calcd: 1436.79 ([M+H]+). Found: 1436.22.

Synthesis Example 7

This example illustrates the synthesis of Compound L6 and Compound B6.

The synthesis was carried out in two steps.

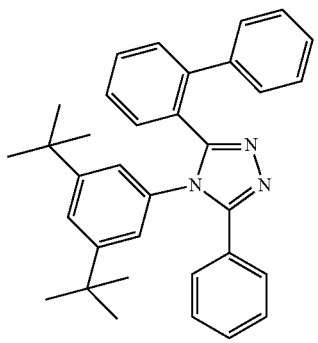 [SMILES: CC(C)(C)c1cc(-n2c(-c3ccccc3)nnc2-c2ccccc2-c2ccccc2)cc(C(C)(C)C)c1]

Step 1. 3-(Biphenyl-2-yl)-4-(3,5-di-tert-butylphenyl)-5-phenyl-4H-1,2,4-triazole, Compound L6

Inside the glovebox, 3,5-di-tert-butylaniline (1.0 g, 4.9 mmol) was added to a 25-ml Schlenk tube containing a stir bar. It was stirred and treated with anhydrous aluminum chloride (0.16 g, 1.2 mmol) in small portions with stirring to give a light tan solution. The mixture was stirred and heated to 140° C. for 2 h. The mixture was treated with 2-(biphenyl-2-yl)-5-phenyl-1,3,4-oxadiazole (0.53 g, 1.8 mmol) followed by anhydrous NMP (0.5 mL) and heated at 210° C. starting at 16 h. The reaction was quenched with water (10 mL) and the product was extracted with ethyl acetate (3×50 mL). Biotage purification was performed to give a semicrystalline white solid (0.70 g, 81%). $^1$H NMR (500 MHz, CD$_2$Cl$_2$) δ 7.80 (m, 1H, ArH), 7.54-7.49 (m, 2H, ArH), 7.32-7.21 (m, 6H, ArH), 7.13 (m, 1H, ArH), 7.10-7.02 (m, 2H, ArH), 6.74 (m, 2H, ArH), 5.99 (s, 2H, ArH), 0.93 (s, 18H, C(CH$_3$)$_3$).

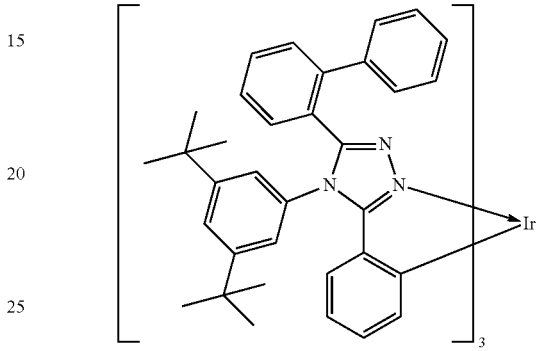

Step 2. Tris{2-[5-(biphenyl-2-yl)-4-(3,5-di-tert-butylphenyl)-4H-1,2,4-triazol-3-yl-κN²]phenyl-κC¹}iridium, Compound B6

3-(Biphenyl-2-yl)-4-(3,5-di-tert-butylphenyl)-5-phenyl-4H-1,2,4-triazole (0.67 g, 1.4 mmol) and iridium acetylacetonate (0.21 g, 0.42 mmol) were combined into a 20-mL scintillation vial and mixed. The mixture was charged into a 6-mL stainless steel tube and brought in to a glovebox and sealed. The solid mixture was heated at 250° C. for 122 h. The crude material was purified by Biotage chromatography and the resulting product was recrystallized in acetone and hexanes to yield a powder (0.11 g, 22%). $^1$H NMR (500 MHz, CD$_2$Cl$_2$) δ 7.97-7.82 (b, 3H, ArH), 7.51-7.44 (b, 6H, ArH), 7.30-7.22 (b, 6H, ArH), 7.14-6.98 (b, 3H, ArH), 6.90-6.30 (b, 30H, ArH), 1.20-0.90 (b, 54H, C(CH$_3$)$_3$). LC/MS (SQ with ESI) C$_{102}$H$_{102}$IrN$_9$ calcd: 1647.1865 ([M+H]+). Found: 1646.48.

Synthesis Example 8

This example illustrates the synthesis of Compound L7 and Compound B7.

The synthesis was carried out in four steps.

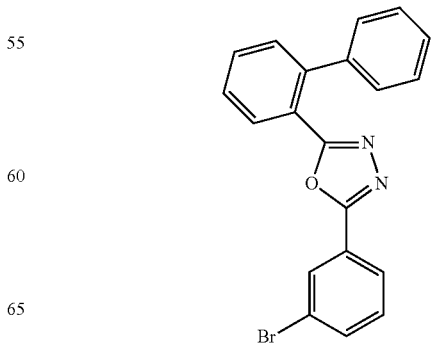

Step 1. 2-Biphenyl-2-yl-5-(3-bromo-phenyl)[1,3,4]oxadiazole

Biphenyl-2-carboxylic acid (5.0 g, 25 mmol) was charged into a 1-L RBF equipped with a stir bar and N₂ bubbler. 3-Bromobenzhydrazide (5.4 g, 25 mmol), acetonitrile (200 mL), Hunig's base (13.2 mL, 75.7 mmol), then O-(benzotriazol-1-yl)-N,N,N',N'-tetramethyluronium tetrafluoroborate (8.7 g, 28 mmol) were added and the resulting mixture was stirred at room temperature. The reaction was monitored by TLC. After approximately 24 h when 3-bromobenzhydrazide was mostly consumed, Hunig's base (8.7 mL) and tosyl chloride (14.4 g, 75.7 mmol) were added. The mixture was stirred. After reaction progress is completed as monitored by TLC, the mixture was concentrated to give ~56 g brown oil. It was dissolved in EtOAc, washed with water and brine. The organic layer was dried over MgSO₄, filtered, concentrated under reduced pressure. Biotage purification was performed to give an oil (4.4 g, 46%). ¹H NMR (500 MHz, CD₂Cl₂) δ 8.17 (dd, J=0.9, 7.8 Hz, 1H, ArH), 7.64-7.58 (m, 4H, ArH), 7.54 (dt, J=1.2, 7.7 Hz, 1H, ArH), 7.48 (dd, J=0.8, 7.7 Hz, 1H, ArH), 7.44-7.39 (m, 3H, ArH), 7.31-7.27 (m, 3H, ArH).

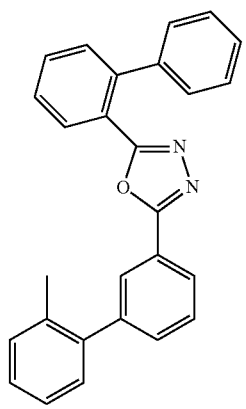 [SMILES: Cc1ccccc1-c1cccc(-c2nnc(-c3ccccc3-c3ccccc3)o2)c1]

Step 2. 2-Biphenyl-2-yl-5-(2'-methyl-biphenyl-3-yl)[1,3,4]oxadiazole

To a 500 mL, 2-neck RBF equipped with a stir bar, condenser, N₂ bubbler and N₂ sparge tube was charged 2-biphenyl-2-yl-5-(3-bromo-phenyl)-[1,3,4]oxadiazole (4.3 g, 11 mmol), o-tolylboronic acid (3.1 g, 23 mmol), K₃PO₄·H₂O (7.9 g, 34 mmol) and toluene (150 mL). The mixture was sparged with N₂ for 30 min. The sparge tube was removed and replaced with a rubber septum, In a dry box, a solution of Pd₂dba₃ (0.21 g, 0.23 mmol) and S-Phos (0.37 g, 0.91 mmol) in toluene (50 mL) was prepared in a sealed RBF. The mixture was stirred at room temperature for 20 min then removed from the dry box and cannula transferred the reaction vessel. The reaction mixture was stirred at 140° C. for 75 min. TLC analysis showed full conversion of the starting oxadiazole. The reaction mixture was diluted with CH₂Cl₂ (100 mL) and passed through a plug of silica gel topped with Celite® followed by CH₂Cl₂ (400 mL) and EtOAc (100 mL). The solution was concentrated under reduced pressure to give an orange oil. Biotage purification was performed with elution of dichloromethane until product began to elute, then slowly added ethyl acetate to flush product off the column to give a foam (2.2 g, 50%). ¹H NMR (500 MHz, CD₂Cl₂) δ 8.16 (m, 1H, ArH), J=0.9, Hz, 1H, ArH), 7.66 (dt, J=1.5, 7.4 Hz, 1H, ArH), 7.60 (dt, J=1.2, 7.5 Hz, 1H, ArH), 7.53 (dt, J=1.1, 7.6 Hz, 1H, ArH), 7.47-7.41 (m, 4H, ArH), 7.33-7.25 (m, 7H, ArH), 7.20 (m, 1H, ArH), 7.16 (d, J=7.0 Hz, 1H, ArH), 2.20 (s, 3H, ArCH₃).

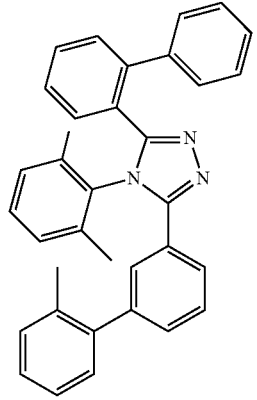 [SMILES: Cc1ccccc1-c1cccc(-c2nnc(-c3ccccc3-c3ccccc3)n2-c2c(C)cccc2C)c1]

Step 3. 3-Biphenyl-2-yl-4-(2,6-dimethyl-phenyl)-5-(2'-methyl-biphenyl-3-yl)4H-[1,2,4]triazole, Compound L7

In a dry box, 2,6-dimethylaniline (1.87 g, 15.4 mmol) and AlCl₃ (0.51 g, 3.9 mmol) to a 25-ml Schlenk tube equipped with a stir bar. The tube was sealed. The mixture was stirred at 140° C. on an aluminum block for 70 min. A solution of 2-biphenyl-2-yl-5-(2'-methyl-biphenyl-3-yl)-[1,3,4]oxadiazole (2.20 g, 5.66 mmol) in NMP (3 mL) was added to the tube. The mixture was stirred at 210° C. for 88 h. The reaction mixture was then diluted with ethyl acetate and washed with water, followed by brine. The organic layer was dried over MgSO₄, filtered, concentrated under reduced pressure to give a dark yellow oil (3.9 g). Biotage purification was performed to give a foam (1.33 g, 48%). ¹H NMR (500 MHz, CD₂Cl₂) δ 7.46-7.43 (m, 2H, ArH), 7.37 (m, 1H, ArH), 7.34-7.21 (m, 7H, ArH), 7.19-7.09 (m, 7H, ArH), 6.90 (d, J=7.4 Hz, ArH), 6.86 (d, J=7.6 Hz, ArH), 1.96 (s, 3H, ArH), 1.54 (s, 3H, ArH), 1.41 (s, 3H, ArH).

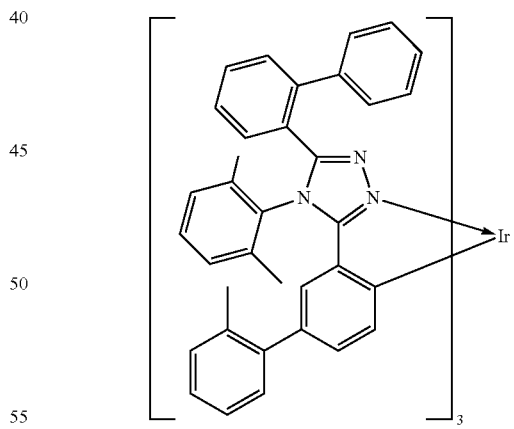

Step 4. Tris{3-[5-(biphenyl-2-yl)-4-(2,6-dimethyl-phenyl)-4H-1,2,4-triazol-3-yl-κN²]-2'-methylbiphenyl-4-yl-κC⁴}iridium A 20-ml scintillation vial was charged with 3-Biphenyl-2-yl-4-(2,6-dimethyl-phenyl)-5-(2'-methyl-biphenyl-3-yl)4H-[1,2,4]triazole (1.2 g, 2.4 mmol) and iridium acetylacetonate (0.36 g, 0.74 mmol) and the mixture transferred to a stainless steel pressure tube. The tube was sealed and heated at 250° C. for 48 h. The product was rinsed from the pressure tube with CH₂Cl₂ and concentrated on rotovap and dried under high vacuum to give 1.3 g brown solid. Biotage purification was performed and the resulting solid (0.87 g) was recrystallized twice from hot EtOAc (10 mL) to give a yellow powder (0.58 g, 47%). $^1$H NMR (500 MHz, CD$_2$Cl$_2$) δ 7.64 (d, J=7.4 Hz, 3H, ArH), 7.49 (dt, J=1.0, 7.6 Hz, 3H, ArH), 7.36 (dt, J=1.0, 7.6 Hz, 3H, ArH), 7.29 (m, 3H, ArH), 7.17 (d, J=7.4 Hz, 6H, ArH), 7.13-7.06 (m, 12H, ArH), 7.03 (m, 3H, ArH), 6.93-6.88 (m, 9H, ArH), 6.82-6.78 (m, 6H, ArH), 6.76-6.70 (m, 6H, ArH), 6.30 (d, J=1.6 Hz, 3H, ArH), 2.00 (s, 9H, C$_6$H$_4$CH$_3$), 1.66 (b, 9H, C$_6$H$_3$(CH$_3$)$_2$), 1.28 (b, 9H, C$_6$H$_3$(CH$_3$)$_2$). LC/MS (SQ with ESI) C$_{105}$H$_{84}$IrN$_9$ calcd: 1664.66 ([M+H]+). Found: 1664.15.

Synthesis Example 9

This example illustrates the synthesis of Compound L8 and Compound B8.

The synthesis was carried out in four steps.

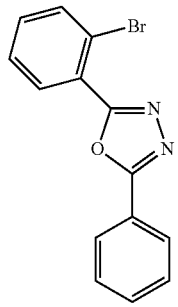 [SMILES: Brc1ccccc1-c1nnc(-c2ccccc2)o1]

Step 1.
2-(2-Bromo-phenyl)-5-phenyl-[1,3,4]oxadiazole

2-Bromobenzoic acid (5.30 g, 26.3 mmol) was charged to a 200-ml round-bottom flask that was equipped with a stir bar and N$_2$ bubbler. Dichloromethane (75 mL) was added via a cannula. Oxalyl chloride (2.3 mL, 28 mmol) was added via a syringe. The reaction mixture was stirred at −5° C. and 2 drops of DMF was added and the mixture was stirred for 25 min. The reaction was allowed to warm to room temperature and stirred for 18.5 h. The reaction mixture was concentrated under reduced pressure and the flask was equipped with a reflux condenser and N$_2$ bubbler. 5-Phenyl-1H-tetrazole (3.85 g, 26.3 mmol) was added, followed by pyridine (30 mL). The reaction mixture was stirred at 90° C. for 4 h. The mixture was concentrated under reduced pressure and purified by Biotage® chromatography to afford a white solid (5.5 g, 69%). $^1$H NMR (500 MHz, CD$_2$Cl$_2$) δ 8.14-8.12 (m, 2H, ArH), 8.03 (dd, J=1.5, 7.8 Hz, 1H, ArH), 7.79 (d, J=8.0 Hz, 1H, ArH), 7.60-7.52 (m, 3H, ArH), 7.50 (m, 1H, ArH), 7.42 (m, 1H, ArH).

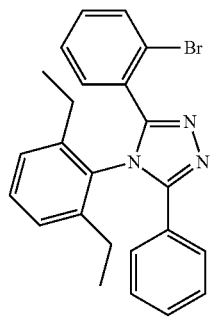 [SMILES: CCc1cccc(CC)c1-n1c(-c2ccccc2)nnc1-c1ccccc1Br]

Step 2. 3-(2-Bromo-phenyl)-4-(2,6-diethyl-phenyl)-5-phenyl-4H-[1,2,4]triazole

In a glove box, 2,6-diethylaniline (6.7 mL, 41 mmol) and AlCl$_3$ (1.4 g, 10 mmol) to a 25-mL Shlenk tube equipped with a stir bar and a male joint cap. The tube was put on a heating block set at 140° C. for 1.5 h with stirring. 2-(2-Bromo-phenyl)-5-phenyl-[1,3,4]oxadiazole (4.5 g, 15 mmol) and NMP (3 mL) were charged and the heating block was set at 210° C. for 65 h. The reaction was allowed to cool to room temperature and then dissolved in ethyl acetate, washed with water and brine. Dried organic layer over MgSO$_4$, filtered, and concentrated under reduced pressure. Biotage® purification was performed to give a colorless powder (1.7 g, 26%). $^1$H NMR (500 MHz, CD$_2$Cl$_2$) δ 7.68 (dd, J=1.1, 8.1 Hz, 1H, ArH), 7.45-7.42 (m, 2H, ArH), 7.38-7.33 (m, 2H, ArH), 7.29-7.25 (m, 2H, ArH), 7.21 (m, 1H, ArH), 7.16 (d, J=7.7 Hz, 2H, ArH), 7.12 (m, 1H, ArH), 6.86 (dd, J=1.6, 7.7 Hz, 1H, ArH), 2.32-2.15 (m, 4H, CH$_2$CH$_3$), 0.90 (t, J=7.5 Hz, CH$_2$CH$_3$). GC/MS (SQ with ESI) C$_{24}$H$_{22}$BrN$_3$ calcd: m/z: 431.10, 433.10 ([M]+). Found: 431, 433.

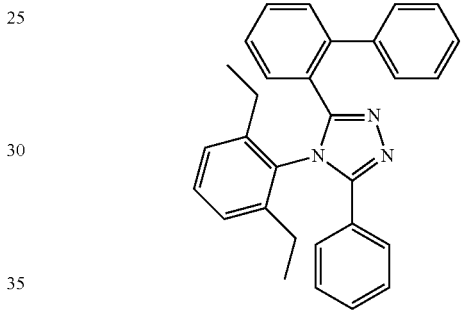

Step 3. 3-Biphenyl-2-yl-4-(2,6-diethyl-phenyl)-5-phenyl-4H-[1,2,4]triazole, Compound L8

To a 200-mL, 2-neck round bottom flask equipped with a stir bar, condenser, N$_2$ bubbler and N$_2$ sparge tube were charged with phenylboronic acid (0.92 g, 7.5 mmol), degassed toluene (30 mL), K$_3$PO$_4$ monohydrate (2.8 g, 12 mmol) and 3-(2-bromo-phenyl)-4-(2,6-diethyl-phenyl)-5-phenyl-4H-[1,2,4]triazole (1.6 g, 3.7 mmol). The mixture was sparged with N$_2$ for 50 min. In a glove box, a solution of Pd$_2$dba$_3$ (0.095 g, 0.10 mmol) and S-Phos (0.17 g, 0.41 mmol) in toluene (10 mL) was prepared in a sealed round bottom flask. The mixture was stirred at room temperature for 20 min and then cannula transferred to the reaction flask. The reaction mixture was stirred with the heating block set to 140° C. for 3 h 40 min. After the mixture was cooled to room temperature, it was diluted with dichloromethane (50 mL) and passed through a plug of Celite® on top of silica. Ethyl acetate (100 mL) was used in to rinse the product from the plug. The filtrate was concentrated under reduced pressure. Biotage® purification was performed to give a white powder (1.6 g), which was recrystallized in boiling ethyl acetate (15 mL) under N$_2$ with stirring. After the addition of 13 ml hexanes, the solution became cloudy. A significant amount of precipitate began to form. Ethyl acetate was added to the boiling solution in 1 mL increments until it became a clear solution. After the addition of ~8 mL the solution was clear. Hexanes (~2 mL) was added dropwise to the boiling solution. The solution was allowed to cool to room temperature and allowed to stand for ~45 minutes. The precipitate was filtered and washed with 1:1 ethyl acetate:hexanes (2×25 mL) and placed under reduced pressure to give a colorless powder (0.90 g, 57%) white powder. $^1$H NMR (500 MHz, CD$_2$Cl$_2$) δ 7.41 (m, 1H, ArH), 7.35-7.18 (m, 14H, ArH), 7.03 (d, J=7.8 Hz, ArH), 1.85 (m, 2H, CH$_2$CH$_3$), 1.76 (m, 2H, CH$_2$CH$_3$), 0.71 (t, J=7.5 Hz, 6H, CH$_2$CH$_3$). LC/MS (SQ with ESI) C$_{30}$H$_{27}$N$_3$ calcd: 430.30 ([M+H]+). Found: 430.53.

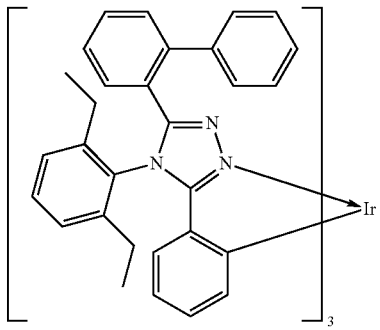

Step 4. Tris(2-{5-(biphenyl-2-yl)-4-[2,6-diethylphenyl]-4H-1,2,4-triazol-3-yl-κN$^2$}phenyl-κC$^1$)iridium, Compound B8

A 20-ml scintillation vial was charged with 3-biphenyl-2-yl-4-(2,6-diethyl-phenyl)-5-phenyl-4H-[1,2,4]triazole (0.85 g, 2.0 mmol) and iridium acetylacetonate (0.30 g, 0.60 mmol) and the mixture transferred to a stainless steel pressure tube. The tube was sealed and heated at 250° C. for 63 h. The product was rinsed from the pressure tube with CH$_2$Cl$_2$ and concentrated on rotovap and dried under high vacuum to give 1.3 g brown solid. Biotage purification was performed and the resulting solid was recrystallized to give a yellow powder (0.25 g, 28%). $^1$H NMR (500 MHz, CD$_2$Cl$_2$, reference peak: CH$_2$Cl$_2$ δ 5.30) δ 7.56 (d, J=7.4 Hz, 3H, ArH), 7.46-7.42 (m, 3H, ArH), 7.31-7.27 (m, 9H, ArH), 7.15 (d, J=7.5 Hz, 6H, ArH), 7.04 (d, J=7.5 Hz, 3H, ArH), 6.99 (d, J=7.5 Hz, 3H, ArH), 6.85-6.76 (m, 9H, ArH), 6.64-6.50 (m, 9H, ArH), 6.18 (d, J=7.4 Hz, 3H, ArH), 2.35-2.27 (m, 3H, ArCH$_2$CH$_3$), 1.99-1.89 (m, 3H, ArCH$_2$CH$_3$), 1.55-1.45 (m, 3H, ArCH$_2$CH$_3$), 1.03-0.93 (m, 3H, ArCH$_2$CH$_3$), 0.77 (t, J=7.5 Hz, 9H, ArCH$_2$CH$_3$), 0.62 (t, J=7.5 Hz, 9H, ArCH$_2$CH$_3$). LC/MS (SQ with ESI) C$_{90}$H$_{78}$IrN$_9$ calcd: 1478.68 ([M+H]+). Found: 1478.49.

Synthesis Example 10

This example illustrates the synthesis of Compound L9 and Compound B9.

The synthesis was carried out in two steps.

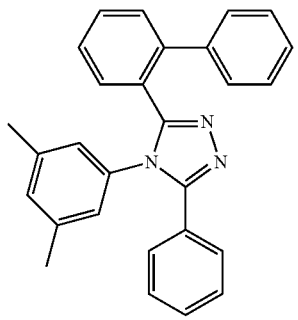 [SMILES: Cc1cc(C)cc(-n2c(-c3ccccc3)nnc2-c2ccccc2-c2ccccc2)c1]

Step 1. 3-(Biphenyl-2-yl)-4-(3,5-dimethylphenyl)-5-phenyl-4H-1,2,4-triazole, Compound L9

Inside the glove box, the 3,5-dimethylaniline (1.14 g, 9.41 mmol) was added to a 25-mL Schlenk tube containing a stir bar. It was stirred and treated with anhydrous aluminum chloride (0.35 g, 2.6 mmol) in small portions with stirring to give a light tan solid. The mixture was stirred at 140° C. for 70 min. The mixture was treated with 2-(biphenyl-2-yl)-5-phenyl-1,3,4-oxadiazole (1.04 g, 3.49 mmol) followed by anhydrous NMP (1.0 mL) and stirred at 210° C. for 16 h, after which the mixture solidified. Water (10 mL) and ethyl acetate (10 mL) were added along with a stir bar to break up the solid. The crude product was extracted with ethyl acetate (50 mL) and washed with brine. Biotage® purification was performed u to give a semi crystalline white solid 1.024 g (73%). $^1$H NMR (500 MHz, CD$_2$Cl$_2$, reference peak: CH$_2$Cl$_2$ δ 5.30) δ 7.70 (dd, J=1.4, 7.5 Hz, 1H, ArH), 7.48 (m, 2H, ArH), 7.31-7.27 (m, 4H, ArH), 7.23-7.12 (m, 5H, ArH), 6.87-6.84 (m, 2H, ArH), 6.79 (s, 1H, ArH), 5.78 (s, 2H, ArH), 1.97 (s, 6H, ArH).

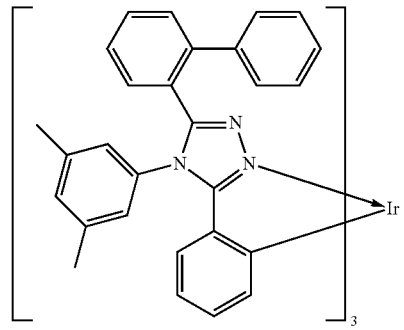

Step 2. Tris{2-[5-(biphenyl-2-yl)-4-(3,5-dimethylphenyl)-4H-1,2,4-triazol-3-yl-κN$^2$]phenyl-κC$^1$}iridium, Compound B9

A 20-ml scintillation vial was charged with 3-(biphenyl-2-yl)-4-(3,5-dimethylphenyl)-5-phenyl-4H-1,2,4-triazole (1.00 g, 2.49 mmol) and iridium acetylacetonate (0.37 g, 0.76 mmol) and the mixture transferred to a stainless steel pressure tube. The tube was sealed and heated at 250° C. for 36 h. The product was rinsed from the pressure tube with CH$_2$Cl$_2$ and concentrated under reduced pressure. The solid (0.20 g) was recrystallized in refluxing acetone under nitrogen and allowed to cool to room temperature slowly to give a yellow powder (0.11 g, 10%). $^1$H NMR (500 MHz, CD$_2$Cl$_2$, reference peak: CH$_2$Cl$_2$ δ 5.30) δ 7.86 (b, 3H, ArH), 7.52-7.40 (b, 6H, ArH), 7.32 (b, 3H, ArH), 7.19 (b, 3H, ArH), 7.00-6.70 (b, 21H, ArH), 6.55 (b, 4H, ArH), 6.35 (b, 4H, ArH), 5.8 (b, 4H, ArH), 2.14-1.93 (b, 6H, CH$_3$). LC-MS (SQ with ESI) C$_{84}$H$_{66}$IrN$_9$ calcd: 1394.78 ([M+H]+). Found: 1395.60.

Synthesis of Comparative Compounds A1 and A2

Comparative Compound A1 was synthesized in four convergent steps as follows:

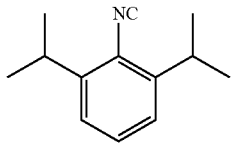

Step 1: Synthesis of 2-isocyano-1,3-diisopropylbenzene

Reference: Weber, W. P.; Gokel, G. W.; Ugi, I. K. *Angew. Chem., Int. Ed.* 1972, 11, 530.

A 2-neck, 500-mL round-bottom flask equipped with a stir bar, thermometer, a nitrogen inlet bubbler and a cooling condenser was charged with 2,6-diisopropyaniline (25 g, 141 mmol), benzyltriethylammonium chloride (0.38 g, 1.7 mmol), chloroform (11.3 mL, 141 mmol), and dichloromethane (35 mL). An aqueous 50% sodium hydroxide solution (45 mL) was then added. The solution was rinsed in with water (5 mL). The mixture was stirred at 25° C. for approximately 4 h, then stirred at 43° C. for 24 h. The reaction mixture was then diluted with deionized water (500 mL) and extracted with dichloromethane (2×250 mL). The organic layers were combined and washed with deionized water, followed by brine, separated and dried over K$_2$CO$_3$, filtered and concentrated under reduced pressure to give a brown oil (26.9 g). The crude oil was purified by flash column chromatography (4:1 hexanes:dichloromethane) to give a dark brown oil (20 g, 75%). $^1$H NMR (500 MHz, CD$_2$Cl$_2$) δ 7.35 (m, 1H, p-ArH), 7.19 (m, 2H, m-ArH), 3.38 (m, 2H, ArCH(CH$_3$)$_2$), 1.28 (d, 12H, ArCH(CH$_3$)$_2$)).

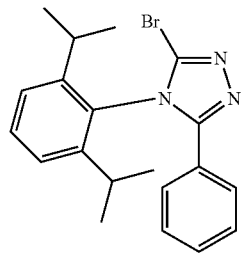 [SMILES: CC(C)c1cccc(C(C)C)c1-n1c(Br)nnc1-c1ccccc1]

Step 2: Synthesis of 3-bromo-4-(2,6-diisopropylphenyl)-5-phenyl-4H-1,2,4-triazole Reference: This is a classic Huisgen rearrangement reaction.

An oven-dried 100-mL round-bottom flask equipped with a stir bar, rubber septum and a nitrogen bubbler was charged with 2-isocyano-1,3-diisopropylbenzene (5 g, 27 mmol) and dichloromethane (60 mL). The flask was placed in a water bath at 25° C. and bromine (1.4 mL, 27 mmol) was added dropwise over a period of 2-3 minutes via a plastic syringe. The flask was removed from the water bath, covered with aluminum foil and stirred at 25° C. for 19 h. Another 100-mL round-bottom flask was charged with 5-phenyl-1H-tetrazole (3.95 g, 27 mmol) in dichloromethane (45 mL). Triethylamine (7.5 mL, 54 mmol) was added via a syringe to this suspension, which became homogeneous. This tetrazole solution was transferred to the other round-bottom flask via a cannula over a period of 2 min. The mixture was stirred at 25° C. for 23 h. The mixture was concentrated under reduced pressure to give a brown sludge. The sludge was dissolved in ethyl acetate (300 mL) and washed with water (2×250 mL) then brine, separated, dried over MgSO$_4$. The resulting imidoyl bromide was purified on a Biotage column chromatography to give 2.2 g of brown oil (20%). This oil was then dissolved in anhydrous toluene and the mixture was refluxed under nitrogen for 1.5 h. The reaction mixture was concentrated under reduced pressure and the crude product was dissolved in a minimal amount of dichloromethane and then passed through a plug of 50 g silica gel by eluting with 1% ethyl acetate in dichloromethane, then 2%, and 5% mixtures to give 1.75 g of an off-white powder (16% overall yield). $^1$H NMR (500 MHz, CD$_2$Cl$_2$) δ 7.60 (m, 1H, ArH), 7.48 (m, 2H, ArH), 7.37 (m, 3H, ArH), 7.28 (m, 2H, ArH), 2.08 (m, 2H, ArCH(CH$_3$)$_2$), 1.20 (d, 6H, ArCH(CH$_3$)$_2$), 0.89 (d, 6H, ArCH(CH$_3$)$_2$).

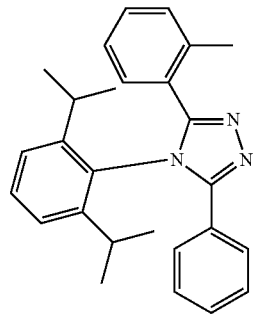 [SMILES: Cc1ccccc1-c1nnc(-c2ccccc2)n1-c1c(C(C)C)cccc1C(C)C]

Step 3: Synthesis of Compound L10, 4-(2,6-diisopropylphenyl)-3-phenyl-5-(o-tolyl)-4H-1,2,4-triazole A 2-neck, 100-mL round-bottom flask equipped with a stir bar, condenser, nitrogen bubbler, and a nitrogen sparge tube was charged with K$_3$PO$_4$ (1.8 g, 7.8 mmol), o-tolyl boronic acid (0.70 g, 5.2 mmol), toluene (40 mL) and 3-bromo-4-(2,6-diisopropylphenyl)-5-phenyl-4H-1,2,4-triazole (1.0 g, 2.6 mmol). The mixture was sparged with nitrogen for 40 min. In a drybox, a round-bottom flask equipped with a stir bar was charged with tris(benzylideneacetone)dipalladium (0.12 g, 0.13 mmol), 2-dicyclohexylphosphino-2',6'-dimethoxybiphenyl (0.21 g, 0.52 mmol) and toluene (15 mL). The dark purple solution was stirred for 20 min. This solution was transfer to the reaction mixture via a cannula and the reaction mixture was refluxed under a nitrogen atmosphere for 15.5 h. The reaction mixture was then diluted with a 1:1 ethylacetate:dichloromethane mixture and filtered through a column. The crude product was concentrated under reduced pressure and purified by Biotage column chromatography to give 0.7 g (75%) of a colorless powder. $^1$H NMR (500 MHz, CD$_2$Cl$_2$) δ 7.60 (m, 1H, ArH), 7.48 (m, 2H, ArH), 7.37 (m, 3H, ArH), 7.28 (m, 2H, ArH), 2.08 (m, 2H, ArCH(CH$_3$)$_2$), 1.20 (d, 6H, ArCH(CH$_3$)$_2$), 0.89 (d, 6H, ArCH(CH$_3$)$_2$).

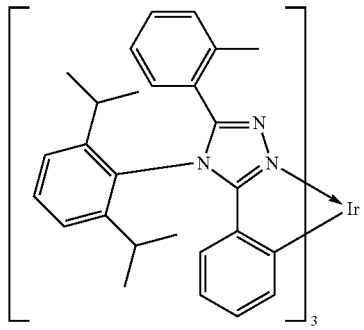

Comparative A1

Step 4: Reaction of Ir(acac)$_3$ with Compound L10 to synthesize compound B10, fac-Tris{N$^2$-κ-C$^2$-(3-(4-(2,6-diisopropylphenyl)-5-(o-tolyl)-4H-1,2,4-triazolyl)phenyl)iridium, Comparative Compound A1, shown above A 10-mL stainless steel pressure tube was charged with a premixed powder containing 4-(2,6-diisopropylphenyl)-3- phenyl-5-(o-tolyl)-4H-1,2,4-triazole (0.69 g, 1.75 mmol) and tris(acetylacetonate)iridium (0.26, 0.53 mmol). The tube was pressured with sparged nitrogen to 0 psig and heated to 250° C. for 3 d during which the pressure reached 170 psig. After cooling to room temperature the crude material was removed from the tube with a spatula and the remaining materials are rinsed with dichloromethane. The materials were concentrated under reduced pressure to give 0.8 g of crude product. Purification was performed by Biotage column chromatography to give 0.360 g of a yellow powder. Further purification was performed on the Biotage to give 0.125 g of a colorless solid (17%) with 99.4% purity by UPLC. $^1$H NMR (500 MHz, CD$_2$Cl$_2$) δ 7.51 (m, 3H, ArH), 7.26 (m, 6H, ArH), 7.23 (m, 3H, ArH), 7.18 (m, 3H, ArH), 6.89 (m, 3H, ArH), 6.84 (m, 6H, ArH), 6.70 (m, 3H, ArH), 6.5 (m, 3H, ArH), 6.19 (m, 3H, ArH), 2.81 (m, 3H, ArCH(CH$_3$)$_2$, 2.31 (s, 12H, ArCH$_3$, 2.29 (m, 3H, ArCH(CH$_3$)$_2$), 0.95 (d, 9H, ArCH(CH$_3$)$_2$), 0.81 (d, 9H, ArCH(CH$_3$)$_2$), 0.77 (d, 9H, ArCH(CH$_3$)$_2$), 0.73 (d, 9H, ArCH(CH$_3$)$_2$).

Comparative Compound A2, shown below, was synthesized in an analogous manner starting with 2,6-dimethylaniline.

Comparative A2

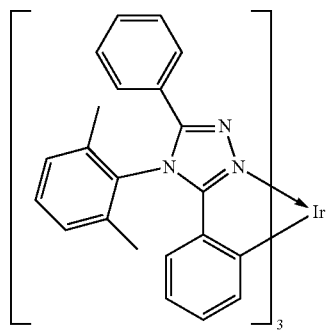

Device Examples

These examples demonstrate the fabrication and performance of OLED devices.
(1) Materials
HIJ-1 is an electrically conductive polymer doped with a polymeric fluorinated sulfonic acid. Such materials have been described in, for example, published U.S. patent applications US 2004/0102577, US 2004/0127637, US 2005/0205860, and published PCT application WO 2009/018009.
HT-1 is a triarylamine-containing polymer. Such materials have been described in, for example, published PCT application WO 2009/067419.
Host-1 is the carbazole-furan derivative shown below

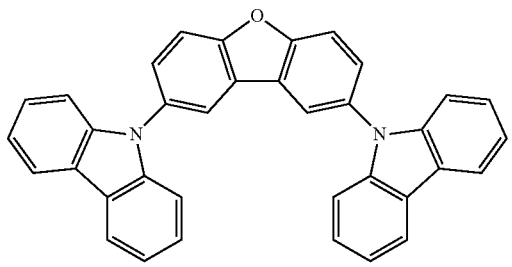 [SMILES: c1ccc2c(c1)c1ccccc1n2-c1ccc2oc3ccc(-n4c5ccccc5c5ccccc54)cc3c2c1]

Host-2 is the carbazole-thiophene derivative shown below

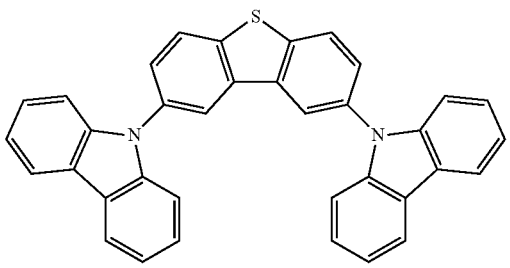 [SMILES: c1ccc2c(c1)c1ccccc1n2-c1ccc2sc3ccc(-n4c5ccccc5c5ccccc54)cc3c2c1]

ET-1 is a metal quinolate complex.
Comparative Compounds A1 and A2 are discussed above.
The devices had the following structure on a glass substrate:
anode=Indium Tin Oxide (ITO), 50 nm
hole injection layer=HIJ-1 (50 nm)
hole transport layer=HT-1 (20 nm)
photoactive layer, discussed below=100:14 Host:dopant ratio (43 nm);
anti-quenching layer=Host-1 or Host-2 (10 nm)
electron transport layer=ET-1 (10 nm)
electron injection layer/cathode=CsF/Al (1/100 nm)
(2) Device Fabrication OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a hole transport solution, and then heated to remove solvent. The substrates were masked and placed in a vacuum chamber. The photoactive layer, the electron transport layer and the anti-quenching layer were deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.
(3) Device Characterization The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

Example 1 and Comparative Example A

This example illustrates the use of Compound B3 and Comparative Compound A1 as the light-emitting material in a device. The results are given in Table 1 below.

TABLE 1

Device results

| Example | Dopant | Host | EL peak (nm) | CIE (x, y) | EQE @1000 nits (%) |
|---|---|---|---|---|---|
| Comparative A | Comp. A1 | Host-2 | 476 | (0.178, 0.369) | 17.80% |
| 1 | B3 | Host-2 | 477 | (0.183, 0.383) | 19.80% |

All data @ 1000 nits. E.Q.E. is the external quantum efficiency;
CIE (x, y) are the x and y color coordinates according to the C.I.E. chromaticity scale (Commission Internationale de L'Eclairage, 1931).

It can be seen from the results that the efficiency is greater in the device with the compound having Formula II, Compound B3, as the light-emitting material.

Example 2 and Comparative Example B

This example illustrates the use of Compound B10 and Comparative Compound A2 as the light-emitting material in a device. The results are given in Table 2 below.

TABLE 2

Device results

| Example | Dopant | Host | EL peak (nm) | CIE (x, y) | EQE @1000 nits (%) |
|---|---|---|---|---|---|
| Comparative B | Comp. A2 | Host-2 | 488 | (0.221, 0.494) | 15.60% |
| 2 | B10 | Host-2 | 469 | (0.173, 0.323) | 18.40% |

All data @ 1000 nits. E.Q.E. is the external quantum efficiency;
CIE (x, y) are the x and y color coordinates according to the C.I.E. chromaticity scale (Commission Internationale de L'Eclairage, 1931).

It can be seen from the results that the efficiency is greater and the color is shifted to a better blue in the device with the compound having Formula II, Compound B10, as the light-emitting material.

Examples 3-10

These examples illustrate the use of compounds having Formula II as the light emitting material in a device.

The materials used and the results are given in Table 3 below.

TABLE 3

Device results

| Example | Dopant | Host | EL peak (nm) | CIE (x, y) | EQE @1000 nits (%) |
|---|---|---|---|---|---|
| 3 | B1 | Host-2 | 477 | (0.187, 0.367) | 15.10% |
| 4 | B2 | Host-2 | 478 | (0.192, 0.406) | 24.10% |
| 5 | B4 | Host-1 | 473 | (0.193, 0.402) | 20.70% |
| 6 | B5 | Host-1 | 471 | (0.195, 0.478) | 16.70% |
| 7 | B6 | Host-1 | 480 | (0.209, 0.464) | 23.30% |
| 8 | B7 | Host-1 | 476 | (0.198, 0.427) | 20.80% |
| 9 | B8 | Host-1 | 472 | (0.179, 0.357) | 22.70% |
| 10 | B9 | Host-1 | 477 | (0.181, 0.371) | 21.90% |
| 11 | B10 | Host-1 | 468 | (0.168, 0.296) | 20.0% |

All data @ 1000 nits. E.Q.E. is the external quantum efficiency;
CIE (x, y) are the x and y color coordinates according to the C.I.E. chromaticity scale (Commission Internationale de L'Eclairage, 1931).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula II

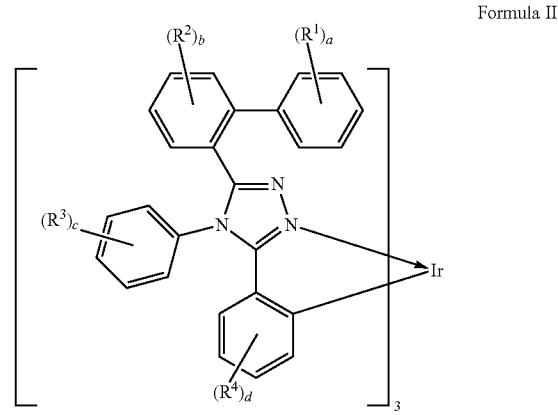

Formula II wherein:
$R^1$-$R^4$ are the same or different at each occurrence and are selected from the group consisting of D, alkyl, silyl, aryl, deuterated alkyl, deuterated silyl, and deuterated aryl;

a and c are the same or different and are an integer from 0-5; and b and d are the same or different and are an integer from 0-4.

2. The compound of claim 1, wherein the compound is at least 10% deuterated.

3. The compound of claim 1, wherein a>0 and $R^1$ is an unsubstituted alkyl or deuterated unsubstituted alkyl having 1-6 carbons.

4. The compound of claim 1, wherein a=0.

5. The compound of claim 1, wherein b>0 and $R^2$ is an unsubstituted alkyl or unsubstituted deuterated alkyl having 1-6 carbons.

6. The compound of claim 1, wherein b=0.

7. The compound of claim 1, wherein c>0 and $R^3$ is an alkyl or deuterated alkyl having 1-6 carbons.

8. The compound of claim 1, wherein c>0 and $R^3$ is a branched alkyl or deuterated branched alkyl having 3-8 carbons.

9. The compound of claim 1, wherein c=1 or 2.

10. The compound of claim 1, wherein c=2 and the $R^3$ groups are meta to each other.

11. The compound of claim 1, wherein d>0 and at least one $R^4$ is an aryl or deuterated aryl having 6-18 ring carbons.

12. The compound of claim 1, wherein d>0 and $R^4$ is an alkylaryl or deuterated alkylaryl having 6-20 carbons.

13. A compound selected from Compound B1 through Compound B10

Compound B1

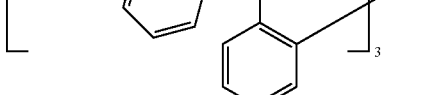

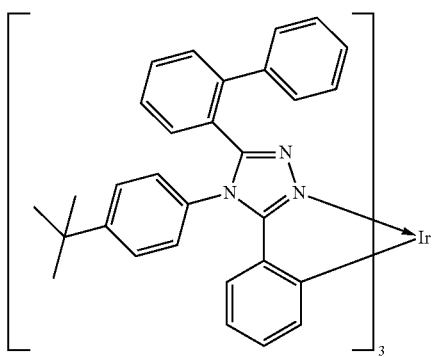

Compound B2

-continued

Compound B3

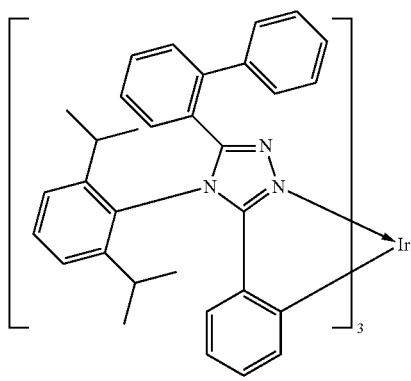

Compound B4

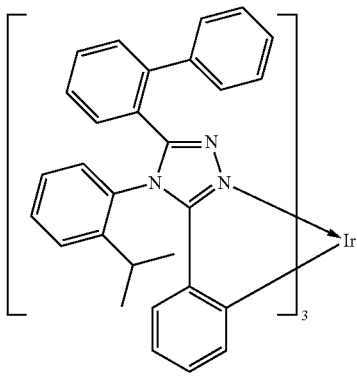

Compound B5

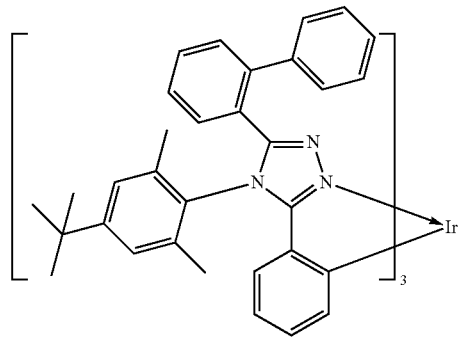

Compound B6

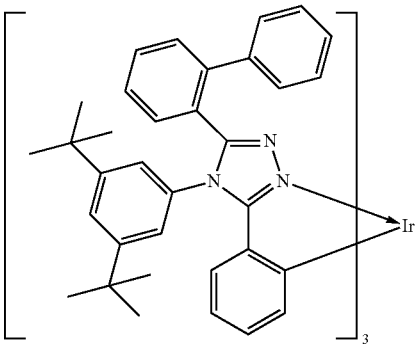

-continued

Compound B7

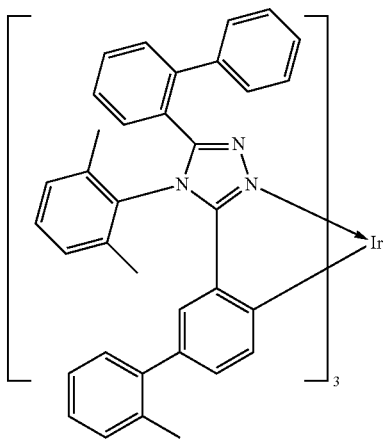

Compound B8

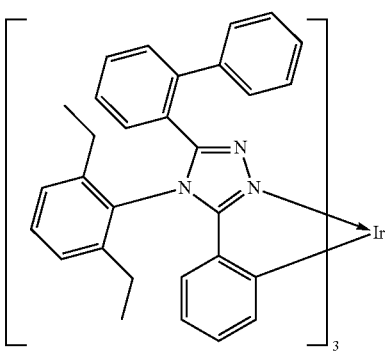

Compound B9

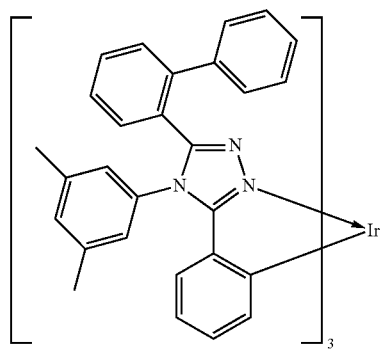

Compound B10

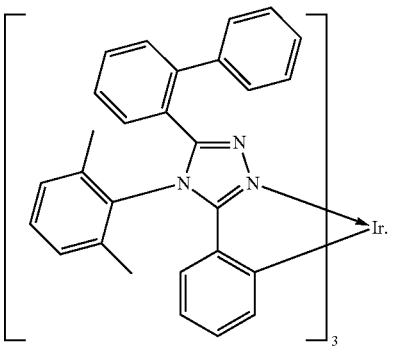

14. An organic electronic device comprising a first electrical contact, a second electrical contact and a photoactive layer therebetween, the photoactive layer comprising a compound having Formula II

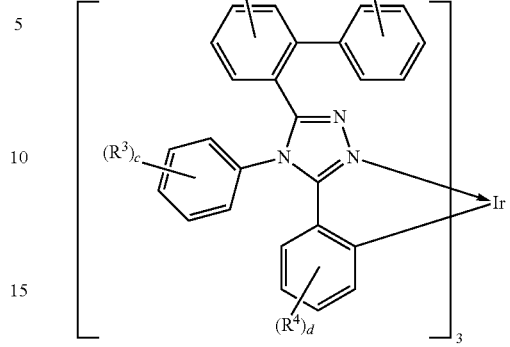

Formula II wherein:
$R^1$-$R^4$ are the same or different at each occurrence and are selected from the group consisting of D, alkyl, silyl, aryl, deuterated alkyl, deuterated silyl, and deuterated aryl;
a and c are the same or different and are an integer from 0-5; and
b and d are the same or different and are an integer from 0-4.

15. The device of claim 14, wherein the photoactive layer comprises the compound of Formula II and further comprises a host material.

16. The device of claim 14, wherein the photoactive layer consists essentially of the compound of Formula II and a host material.

17. A compound having Formula I

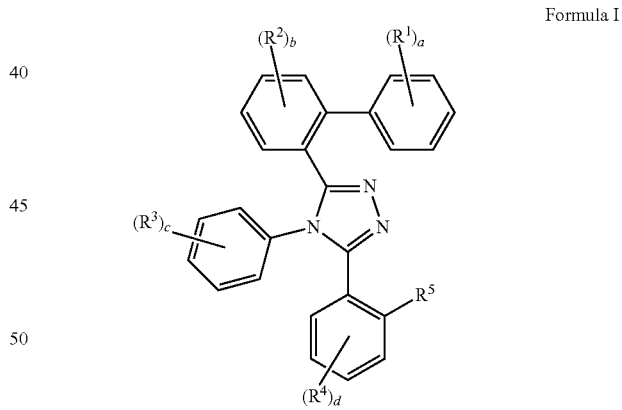

Formula I wherein:
$R^1$-$R^4$ are the same or different at each occurrence and are selected from the group consisting of D, alkyl, silyl, aryl, deuterated alkyl, deuterated silyl, and deuterated aryl;
$R^5$ is H or D;
a and c are the same or different and are an integer from 0-5; and
b and d are the same or different and are an integer from 0-4.

* * * * *